US 8,761,518 B2

(12) United States Patent
Inoue et al.

(10) Patent No.: US 8,761,518 B2
(45) Date of Patent: Jun. 24, 2014

(54) PATTERN INSPECTION APPARATUS

(75) Inventors: Hiromu Inoue, Kanagawa-ken (JP);
Takeshi Fujiwara, Kanagawa-ken (JP);
Hiroshi Tsukada, Kanagawa-ken (JP);
Takashi Hirano, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 360 days.

(21) Appl. No.: 13/183,792

(22) Filed: Jul. 15, 2011

(65) Prior Publication Data

US 2012/0020546 A1    Jan. 26, 2012

(30) Foreign Application Priority Data

Jul. 16, 2010  (JP) ................................. 2010-162316

(51) Int. Cl.
*G06K 9/48* (2006.01)

(52) U.S. Cl.
USPC ........... 382/199; 382/209; 382/190; 382/208; 382/181; 382/218

(58) Field of Classification Search
None
See application file for complete search history.

(56) References Cited

U.S. PATENT DOCUMENTS

| | | | | |
|---|---|---|---|---|
| 6,141,040 | A * | 10/2000 | Toh ................................ | 348/126 |
| 7,664,608 | B2 * | 2/2010 | Urano et al. ...................... | 702/40 |
| 2002/0114506 | A1 * | 8/2002 | Hiroi et al. ...................... | 382/149 |
| 2007/0201044 | A1 * | 8/2007 | Yamane ......................... | 356/636 |
| 2008/0226156 | A1 * | 9/2008 | Ota ............................... | 382/141 |
| 2011/0311126 | A1 * | 12/2011 | Sakai et al. ..................... | 382/149 |

FOREIGN PATENT DOCUMENTS

| | | | |
|---|---|---|---|
| JP | 08-320294 A | 12/1996 | |
| JP | 9-89794 | 4/1997 | |
| JP | 10-253544 | 9/1998 | |
| JP | 11-014323 A | 1/1999 | |
| JP | 2004-145152 | 5/2004 | |
| JP | 2006-30518 A | 2/2006 | |
| JP | 2007-3459 | 1/2007 | |
| JP | 2007-155610 | 6/2007 | |
| JP | 2007-520755 | 7/2007 | |
| JP | 2008-2935 | 1/2008 | |
| JP | 2009-20534 | 1/2009 | |
| JP | WO/2010/086940 | * 10/2009 | ........... G01N 21/956 |
| JP | 2010-71893 | 4/2010 | |

OTHER PUBLICATIONS

Office Action issued Apr. 26, 2013, in Korean Patent Application No. 10-2011-0069988 with English translation.

(Continued)

*Primary Examiner* — Jason M Repko
*Assistant Examiner* — David Perlman
(74) *Attorney, Agent, or Firm* — Oblon, Spivak, McClelland, Maier & Neustadt, L.L.P.

(57) ABSTRACT

According to one embodiment, a pattern inspection apparatus includes a first inspection data creation section, a first delay section, a first recognition section, a first extraction section, a first and a second level difference calculation section, a first and a second determination section, and a first logic OR calculation section. The first extraction section extracts data of a sub-resolution pattern from the first inspection data and the first delay data. The first and second level difference calculation section calculate differences between an average output level of a surrounding region for a target pixel of the extracted data from the first inspection data or the first delay data and an output level of the extracted data. The first and second determination sections determine presence or absence of a defect. The first logic OR calculation section calculates logic OR of determination results of the first and second determination sections.

5 Claims, 28 Drawing Sheets

(56) References Cited

OTHER PUBLICATIONS

Korean Office Action issued Nov. 19, 2012, in Patent Application No. 10-2011-0069988 (with English-language translation).
U.S. Appl. No. 13/798,708, filed Mar. 13, 2013, Inoue, et al.
Office Action issued Apr. 12, 2013 in Korean Patent Application No. 10-2013-0006677 with English language translation.
Office Action issued Jun. 6, 2013, in Japanese Patent Application No. 2010-162316 (with English-language translation).
Amir Sagiv et al. "INTENCD™: Mask Critical Dimension Variation Mapping", Proc. Of SPIE, vol. 7028, (2008), pp. 70282x-1-70282x-12.
Office Action issued in Japanese Patent Application No. 2012-258044 (with English-language translation).

* cited by examiner

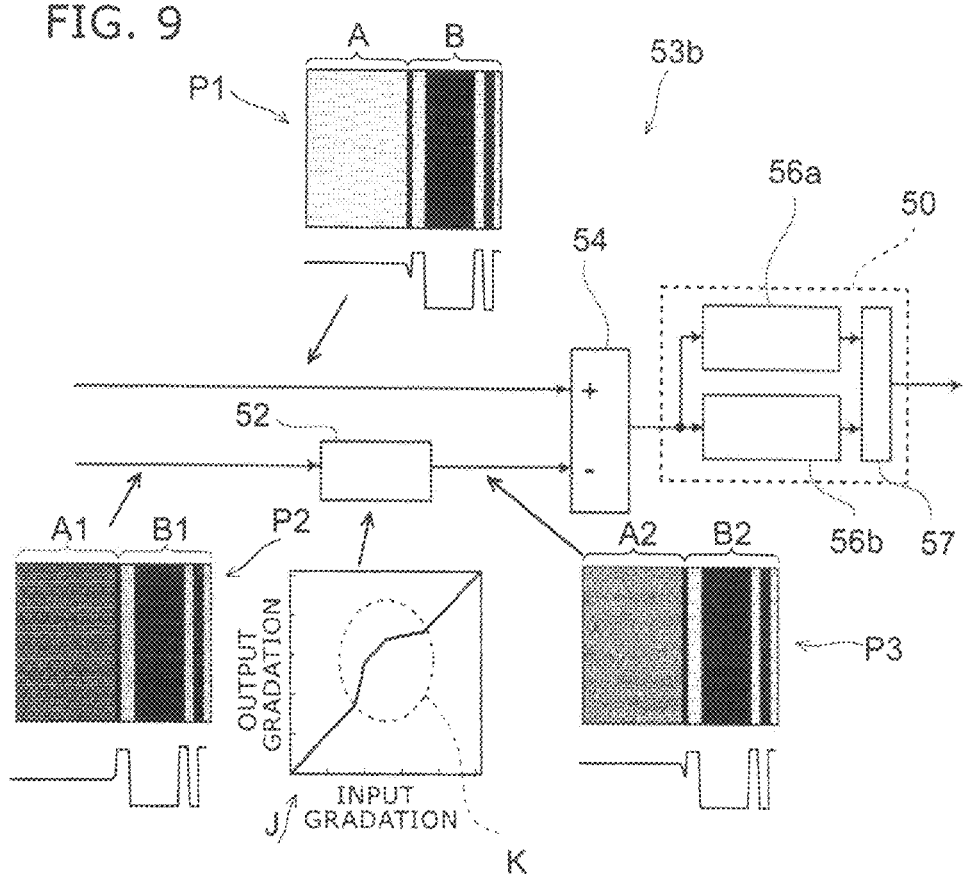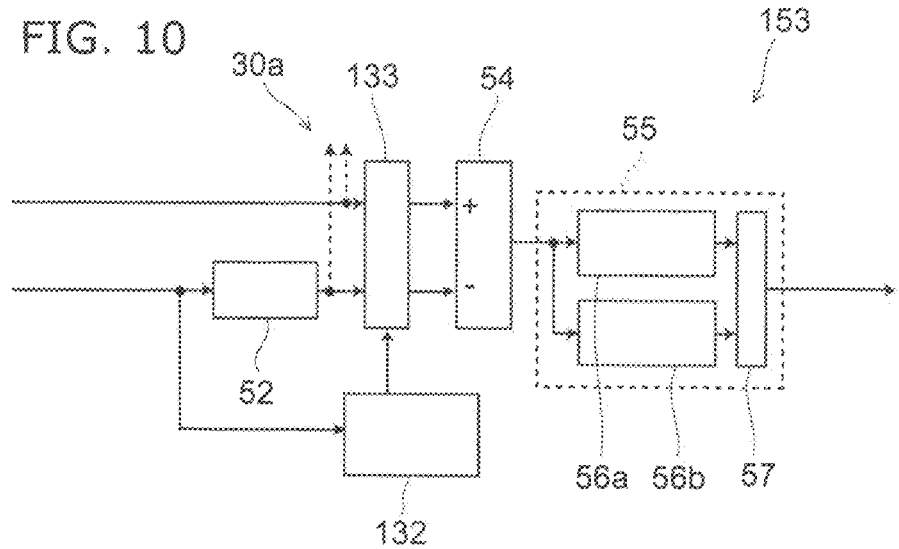

PATTERN INSPECTION APPARATUS

CROSS-REFERENCE TO RELATED APPLICATIONS

This application is based upon and claims the benefit of priority from the prior Japanese Patent Application No. 2010-162316, filed on Jul. 16, 2010; the entire contents of which are incorporated herein by reference.

FIELD

Embodiments described herein relate generally to a pattern inspection apparatus.

BACKGROUND

As a method for inspecting a pattern formed on the surface of a structure, the die-to-die method and die-to-database method are known.

These inspection methods use inspection data obtained by imaging a magnified optical image of the pattern on the light receiving surface of e.g. a CCD sensor (charge coupled device image sensor).

However, recently, pattern miniaturization has advanced, and often made it impossible to optically resolve the pattern. Thus, inspection of such an optically unresolvable pattern may fail to achieve sufficient inspection sensitivity.

BRIEF DESCRIPTION OF THE DRAWINGS

FIG. 9 is a schematic view for illustrating the operation of the reflection inspection section;

FIG. 10 is a block diagram for illustrating an inspection section according to an alternative embodiment;

DETAILED DESCRIPTION

Figure 1:
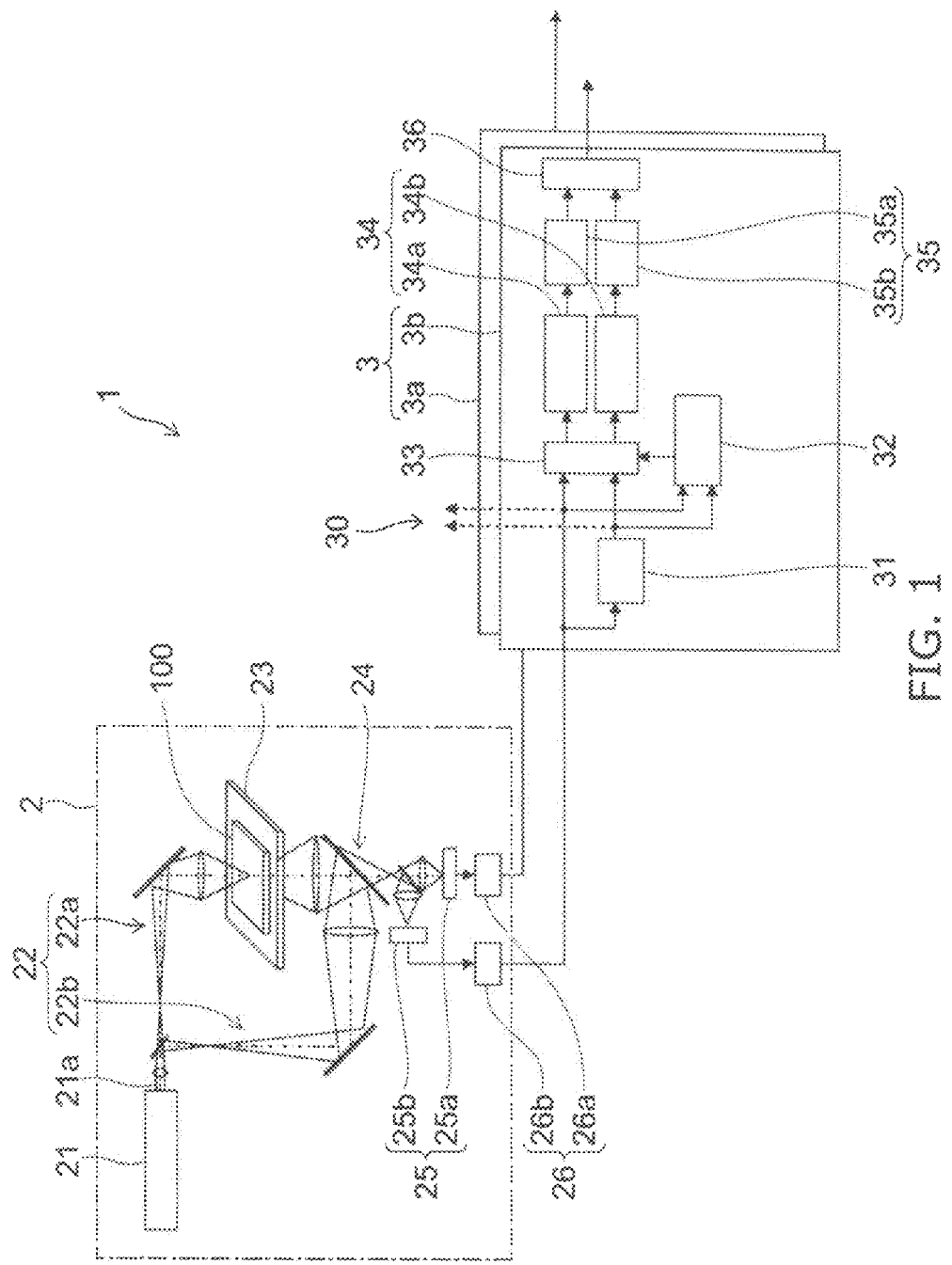
FIG. 1 is a block diagram for illustrating a pattern inspection apparatus according to a first embodiment.

In general, according to one embodiment, a pattern inspection apparatus includes a first inspection data creation section, a first delay section, a first recognition section, a first extraction section, a first level difference calculation section, a second level difference calculation section, a first determination section, a second determination section, and a first logic OR calculation section. The first inspection data creation section is configured to create first inspection data based on an optical image of a pattern formed on a to-be-inspected object.

The first delay section is configured to create first delay data by delaying the first inspection data. The first recognition section is configured to recognize whether or not the first inspection data and the first delay data inputted to the first recognition section are data concerning an image of a sub-resolution pattern. The first extraction section is configured to extract data of the sub-resolution pattern from the first inspection data and the first delay data based on a recognition result of the first recognition section. The first level difference calculation section is configured to calculate an average of an output level of a surrounding region for a target pixel of the extracted data from the first inspection data, and to calculate a difference between an output level of a target pixel of the extracted data from the first inspection data and the average of an output level of a surrounding region for a target pixel. The second level difference calculation section is configured to calculate an average of an output level of a surrounding region for a target pixel of the extracted data for the first delay data, and to calculate a difference between an output level of a target pixel of the extracted data for the first delay data and the average of an output level of a surrounding region for a target pixel. The first determination section is configured to determine presence or absence of a defect based on a calculation result of the first level difference calculation section. The second determination section is configured to determine presence or absence of a defect based on a calculation result of the second level difference calculation section. The first logic OR calculation section is configured to calculate logic OR of a determination result of the first determination section and a determination result of the second determination section.

Various embodiments will be described hereinafter with reference to the accompanying drawings. In the drawings, similar components are labeled with like reference numerals, and the detailed description thereof is omitted as appropriate.

[First Embodiment]

FIG. 1 is a block diagram for illustrating a pattern inspection apparatus according to a first embodiment. As an example, FIG. 1 illustrates a pattern inspection apparatus for inspecting a pattern using the die-to-die method.

As shown in FIG. 1, the pattern inspection apparatus 1 includes a inspection data creation section 2 (first inspection data creation section) and an inspection section 3.

The inspection data creation section 2 includes a light source 21, an illumination optical system 22, a mounting section 23, an imaging optical system 24, a detection section 25, and a conversion section 26.

The inspection data creation section 2 creates inspection data (first inspection data) based on the optical image of a pattern formed on a to-be-inspected object 100. The inspection data creation section 2 can create inspection data based on transmitted light and inspection data based on reflected light.

The light source 21 emits inspection light 21a. As the light source 21, various light sources emitting e.g. white light, monochromatic light, or coherent light can be used. Here, to inspect a fine pattern, it is preferable that the light source 21 can emit inspection light 21a with short wavelength. Examples of such a light source 21 can include a YAG laser light source emitting inspection light 21a with a wavelength of 266 nm. However, the light source is not limited to laser light sources, but can be suitably modified depending on e.g. the size of the pattern.

The illumination optical system 22 includes a transmission illumination optical system 22a and a reflection illumination optical system 22b.

The transmission illumination optical system 22a and the reflection illumination optical system 22b can include various optical elements such as lenses and mirrors.

The type, arrangement, number and the like of the optical elements provided in the transmission illumination optical system 22a and the reflection illumination optical system 22b are not limited to those illustrated, but can be suitably modified. For instance, other optical elements such as a diaphragm, beam splitter, magnification changer, and zoom mechanism can also be provided as appropriate.

The transmission illumination optical system 22a guides the inspection light 21a emitted from the light source 21 to the front side of the to-be-inspected object 100 to generate transmitted light from the inspection region of the to-be-inspected object 100.

The reflection illumination optical system 22b guides the inspection light 21a emitted from the light source 21 to the back side of the to-be-inspected object 100 to generate reflected light from the inspection region of the to-be-inspected object 100.

Furthermore, the transmission illumination optical system 22a and the reflection illumination optical system 22b control the size of the irradiated portion in the inspection region.

The mounting section 23 mounts and holds the to-be-inspected object 100. Furthermore, the mounting section 23 is provided with a moving unit, not shown, so that the inspected position can be changed by moving the position of the to-be-inspected object 100 mounted on the mounting section 23. Here, the moving unit, not shown, does not necessarily need to be provided on the mounting section 23 as long as the inspected position is relatively changed. For instance, the moving unit, not shown, may be configured to change the position of e.g. the illumination optical system 22, the imaging optical system 24, and the detection section 25.

The imaging optical system 24 can include various optical elements such as lenses and mirrors.

The type, arrangement, number and the like of the optical elements provided in the imaging optical system 24 are not limited to those illustrated, but can be suitably modified. For instance, other optical elements such as a diaphragm, beam splitter, magnification changer, and zoom mechanism can also be provided as appropriate. The imaging optical system 24 guides the transmitted light and reflected light from the to-be-inspected object 100 to the light receiving surface of the detection section 25 and images an optical image on the light receiving surface.

In some cases, the pattern may have a dimension shorter than the wavelength of the inspection light 21a and cannot be optically resolved. In such cases, the image of the optically unresolvable pattern (hereinafter also referred to as a sub-resolution pattern) is imaged on the light receiving surface of the detection section 25. For instance, consider the case of a line-and-space pattern, where the wavelength of the inspection light 21a is 193 nm, and the numerical aperture NA is 0.8. Then, a pattern having a pitch dimension (L+S) of 48 nm is an optically unresolvable pattern (sub-resolution pattern), because the pitch dimension is less than half the wavelength of the inspection light 21a.

The detection section 25 includes a detection section 25a for receiving the transmitted light, and a detection section 25b for receiving the reflected light. The detection section 25a, 25b outputs an electrical signal in response to the intensity of light incident on the light receiving surface.

Examples of the detection section 25a, 25b can include a CCD (charge coupled device) line sensor, CCD area sensor, and TDI (time delay and integration) sensor (accumulation type sensor). However, the detection section 25a, 25b is not limited thereto, but a sensor capable of photoelectrically converting the incident light can be suitably selected.

The conversion section 26 includes conversion sections 26a, 26b.

The conversion section 26a A/D converts the electrical signal outputted from the detection section 25a. Furthermore, by converting the A/D converted electrical signal to image data, the conversion section 26a creates inspection data.

The conversion section 26b A/D converts the electrical signal outputted from the detection section 25b. Furthermore, by converting the A/D converted electrical signal to image data, the conversion section 26b creates inspection data.

The inspection section 3 includes a transmission inspection section 3a for performing inspection using inspection data based on transmitted light, and a reflection inspection section 3b for performing inspection using inspection data based on reflected light.

The elements provided in the transmission inspection section 3a can be made similar to the elements provided in the reflection inspection section 3b. Thus, by way of example, the elements provided in the reflection inspection section 3b are illustrated.

The reflection inspection section 3b includes a delay section 31 (first delay section), a recognition section 32 (first recognition section), an extraction section 33 (first extraction section), an level difference calculation section 34, a determination section 35, and a logic OR calculation section 36 (first logic OR calculation section).

As described above, the pattern inspection apparatus 1 inspects a pattern using the die-to-die method. Thus, in the delay section 31, reference data to be compared is created.

For instance, the delay section 31 creates data to be compared (hereinafter referred to as delay data) by delaying the inputted inspection data by the amount of the repetition pitch of the pattern. That is, the delay section 31 creates delay data (first delay data) by inserting a certain time delay in the transfer of the inputted inspection data without changing the waveform of its electrical signal. Then, the delay section 31 outputs the created delay data toward the recognition section 32 and the extraction section 33.

The recognition section 32 receives as input the inspection data and the delay data.

The recognition section 32 recognizes whether or not the inspection data and the delay data inputted thereto are data concerning the image of the aforementioned sub-resolution pattern.

Figure 2:
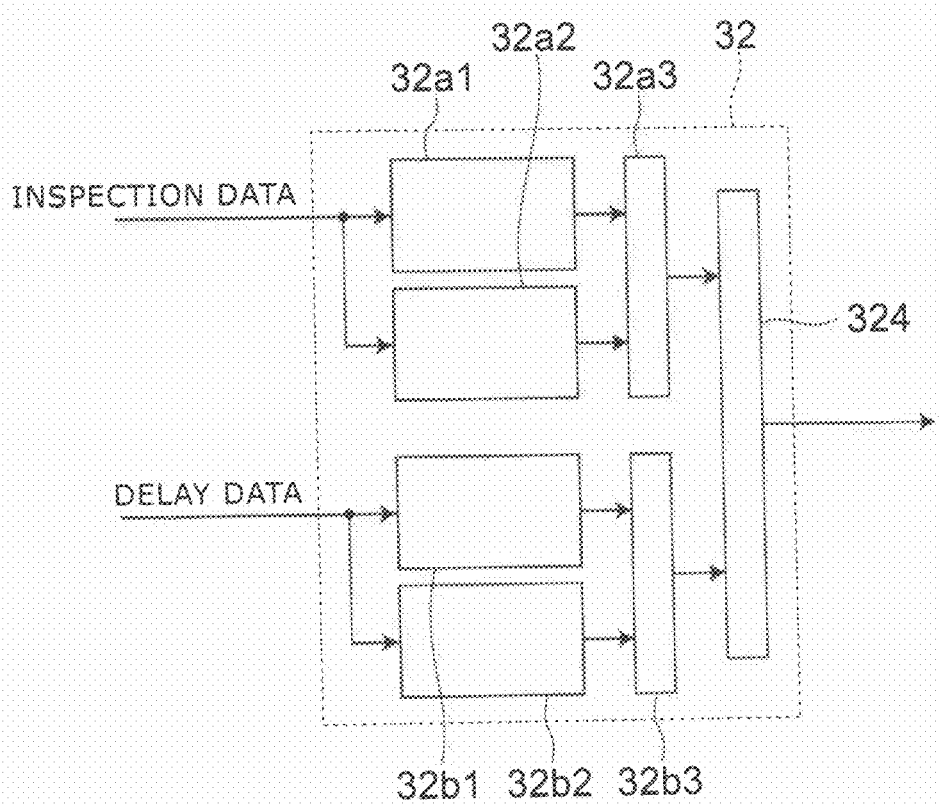
FIG. 2 is a block diagram for illustrating the recognition section.

FIG. 2 is a block diagram for illustrating the recognition section.

As shown in FIG. 2, the recognition section 32 includes determination sections 32a1, 32a2, 32b1, 32b2, logic AND calculation sections 32a3, 32b3, and a logic OR calculation section 324.

The determination sections 32a1, 32a2 make a determination on the inputted inspection data using two thresholds of an upper bound and a lower bound. For instance, the determination section 32a1 can make a determination using the threshold of the lower bound. The determination section 32a2 can make a determination using the threshold of the upper bound.

The determination sections 32b1, 32b2 make a determination on the inputted delay data using two thresholds of an upper bound and a lower bound. For instance, the determination section 32b1 can make a determination using the threshold of the lower bound. The determination section 32b2 can make a determination using the threshold of the upper bound.

FIGS. 3A to 3E are schematic views for illustrating a method for determining whether or not the given data is data concerning the image of a sub-resolution pattern.

Figure 3A:
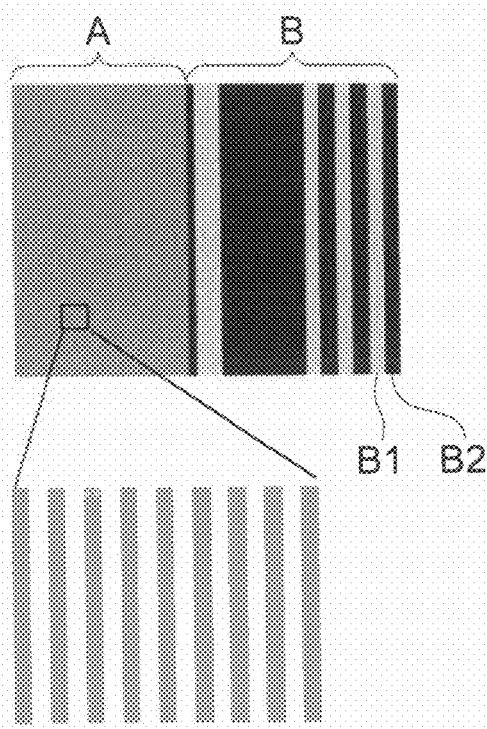
FIG. 3A is a schematic view for illustrating an optically resolved pattern and a sub-resolution pattern.
Figure 3B:
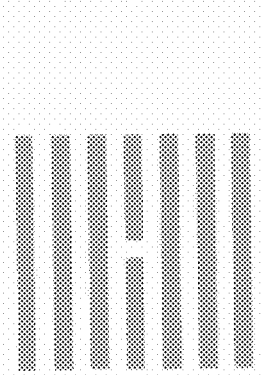
FIG. 3B is a schematic enlarged view for illustrating the sub-resolution pattern.
Figures 3C, 3D:
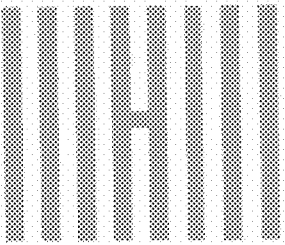
FIG. 3C is a schematic enlarged view for illustrating a so-called open defect on the pattern.
FIG. 3D is a schematic enlarged view for illustrating a so-called short defect on the pattern.
Figure 3E:
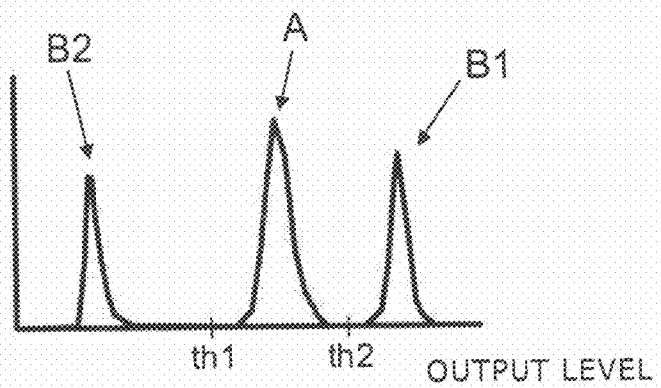
FIG. 3E is a schematic graph for illustrating the relationship between the pattern and the output level.

More specifically, FIG. 3A is a schematic view for illustrating an optically resolved pattern and a sub-resolution pattern. FIG. 3B is a schematic enlarged view for illustrating the sub-resolution pattern. FIG. 3C is a schematic enlarged view for illustrating a so-called open defect on the pattern. FIG. 3D is a schematic enlarged view for illustrating a so-called short defect on the pattern. FIG. 3E is a schematic graph for illustrating the relationship between the pattern and the output level (the output level of the inspection data or the delay data).

As shown in FIG. 3A, in the sub-resolution pattern, the image of the pattern is not resolved. Hence, even if such a pattern as shown in FIG. 3B exists, the pattern results in an image having a generally uniform distribution as shown in the portion A in the figure. On the other hand, in an optically resolved pattern, the image of the pattern is resolved. Here, by way of example, consider the case where a striped pattern as shown in the portion B in the figure is resolved.

In this case, in the striped pattern, the output level of the light portion B1 is higher than the output level of the dark portion B2. In general, the output level of the portion A lies between the output level of the light portion B1 and the output level of the dark portion B2.

This results in the relationship among the light portion B1, the dark portion B2, and the portion A as shown in FIG. 3E. Hence, the optically resolved pattern and the sub-resolution pattern can be recognized from each other.

Here, the sub-resolution pattern has a generally uniform distribution. Hence, by using the threshold th1 of the lower bound and the threshold th2 of the upper bound, accuracy of the recognition can be improved. The threshold th1 and threshold th2 can be previously determined by e.g. experiment or simulation.

The logic AND calculation section 32a3 calculates the logic AND of the determination results of the determination sections 32a1, 32a2. Thus, it can be recognized whether or not the inputted inspection data is data concerning the image of a sub-resolution pattern.

The logic AND calculation section 32b3 calculates the logic AND of the determination results of the determination sections 32b1, 32b2. Thus, it can be recognized whether or not the inputted delay data is data concerning the image of a sub-resolution pattern.

In the foregoing example, the output level of the portion A lies between the output level of the light portion B1 and the output level of the dark portion B2. However, the output levels are not limited thereto. For instance, the output level of the portion A may be higher than the output level of the light portion B1, or the output level of the portion A may be lower than the output level of the dark portion B2. Even in such cases, the optically resolved pattern and the sub-resolution pattern can be similarly recognized from each other.

The logic OR calculation section 324 calculates the logic OR of the recognition result of the logic AND calculation section 32a3 and the recognition result of the logic AND calculation section 32b3. If at least one of the recognition result of the logic AND calculation section 32a3 and the recognition result of the logic AND calculation section 32b3 is a recognition result representing a sub-resolution pattern, the logic OR calculation section 324 outputs a "recognition flag" toward the extraction section 33.

As described above, the waveform of the electrical signal of the inspection data is identical to the waveform of the electrical signal of the delay data. Hence, logic OR calculation by the logic OR calculation section 324 ensures an appropriate recognition even in the case where one of the data is significantly impaired or the output level is varied due to e.g. process conditions. That is, if the thresholds are appropriately specified, it can be appropriately recognized whether or not the given pattern is a sub-resolution pattern from the recognition result based on at least one of the data.

In response to input of the "recognition flag" from the logic OR calculation section 324, the extraction section 33 outputs the corresponding inspection data and delay data toward the level difference calculation section 34. That is, the inspection data and delay data recognized as data of a sub-resolution pattern are outputted toward the level difference calculation section 34.

The level difference calculation section 34 includes an level difference calculation section 34a (first level difference calculation section) for performing calculation on the inspection data inputted through the extraction section 33, and an level difference calculation section 34b (second level difference calculation section) for performing calculation on the delay data inputted through the extraction section 33. The level difference calculation section 34a has the function of calculating the average of the output level of the surrounding region for a target pixel (a target portion in the pattern inspection) of the inputted inspection data. Furthermore, the level difference calculation section 34a has the function of calculating the difference between the output level of the inputted inspection data and the average of the output level of the surrounding region for a target pixel.

The level difference calculation section 34b has the function of calculating the average of the output level of the surrounding region for a target pixel of the inputted delay data. Furthermore, the level difference calculation section 34b has the function of calculating the difference between the output level of the inputted delay data and the average of the output level of the surrounding region for a target pixel.

The determination section 35 includes a determination section 35a (first determination section) for determining the presence or absence of a defect based on the input from the level difference calculation section 34a, and a determination section 35b (second determination section) for determining the presence or absence of a defect based on the input from the level difference calculation section 34b.

Figure 4A:
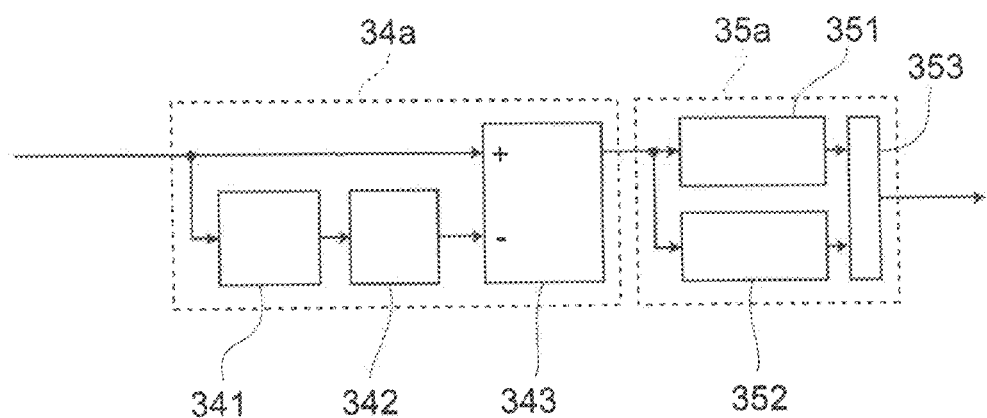
FIG. 4A is a block diagram for illustrating the level difference calculation section, the determination section, and the logic OR calculation section.
Figure 4B:
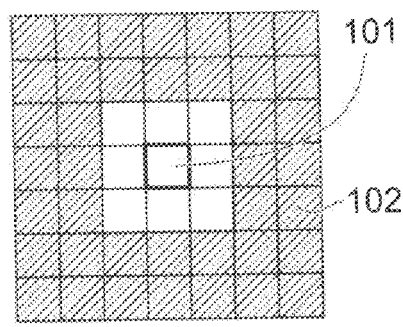
FIG. 4B is a schematic view for illustrating the target pixel and the surrounding region.

FIGS. 4A and 4B are schematic views for illustrating the level difference calculation section, the determination section, and the logic OR calculation section.

More specifically, FIG. 4A is a block diagram for illustrating the level difference calculation section, the determination section, and the logic OR calculation section. FIG. 4B is a schematic view for illustrating the target pixel and the surrounding region.

The level difference calculation section 34a and the determination section 35a can be made similar in configuration to the level difference calculation section 34b and the determination section 35b, respectively. Hence, by way of example, the level difference calculation section 34a and the determination section 35a are illustrated below.

As shown in FIG. 4A, the level difference calculation section 34a includes a surrounding region extraction section 341, an average calculation section 342, and a level difference calculation section 343.

The surrounding region extraction section 341 extracts a surrounding region 102 for the target pixel 101 of the inputted inspection data.

For instance, as illustrated in FIG. 4B, the surrounding region extraction section 341 extracts a surrounding region 102 for the target pixel 101, i.e., the target portion in the pattern inspection, of the inputted inspection data. The position, size, shape and the like of the surrounding region 102 can be previously specified, or can be changed as appropriate.

The average calculation section 342 calculates the average of the output level of the surrounding region 102 for the target pixel 101 extracted by the surrounding region extraction section 341.

The level difference calculation section 343 calculates the difference between the average of the output level of the surrounding region 102 for the target pixel 101 calculated by the average calculation section 342 and the output level of the target pixel 101 of the inputted inspection data.

The determination section 35a includes a determination section 351, a determination section 352, and a logic OR calculation section 353.

The determination section 351, 352 determines the presence or absence of a defect using two thresholds of the upper bound and the lower bound on the data inputted through the level difference calculation section 343. Here, for instance, the determination section 351 can determine the presence or absence of a defect using the threshold of the lower bound. The determination section 352 can determine the presence or absence of a defect using the threshold of the upper bound. In this case, the determination section 351, 352 can determine that a defect is present when the associated threshold is exceeded.

The logic OR calculation section 353 calculates the logic OR of the determination results of the determination sections 351, 352. Thus, the logic OR calculation section 353 outputs a "defect presence flag" toward the logic OR calculation section 36 when at least one of the determination results of the determination sections 351, 352 is a determination result representing the presence of a defect.

The foregoing description refers to the level difference calculation section 34a and the determination section 35a. On the other hand, in the level difference calculation section 34b and the determination section 35b, the delay data is inputted instead of the aforementioned inspection data. Then, in a similar manner to the foregoing, the presence or absence of a defect is determined on the delay data.

FIGS. 5A to 5D are schematic views for illustrating the effect of providing the level difference calculation section.

Figure 5A:
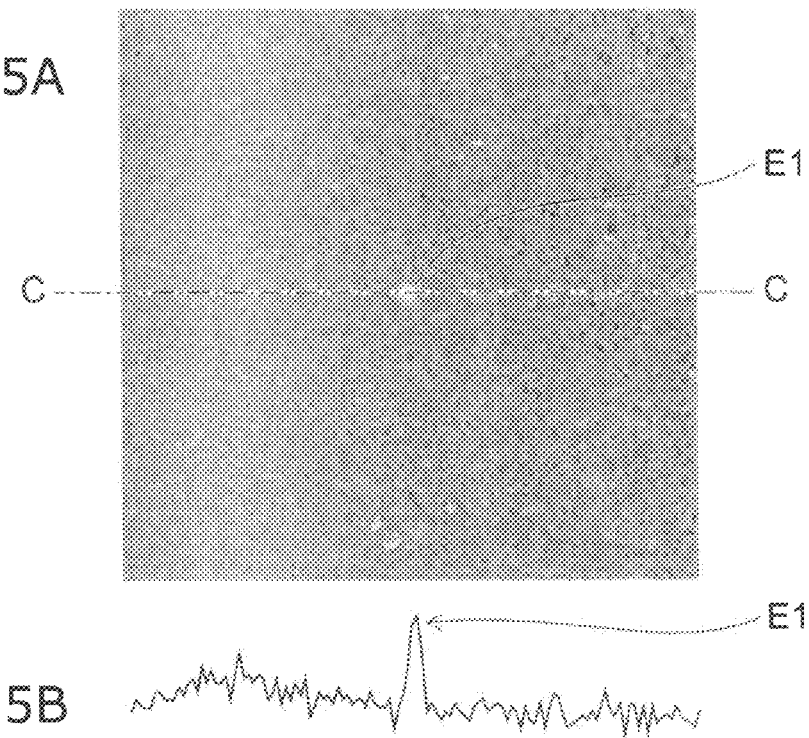
FIGS. 5A and 5B show the case where no level difference calculation section is provided.
Figure 5B:
Figure 5C:
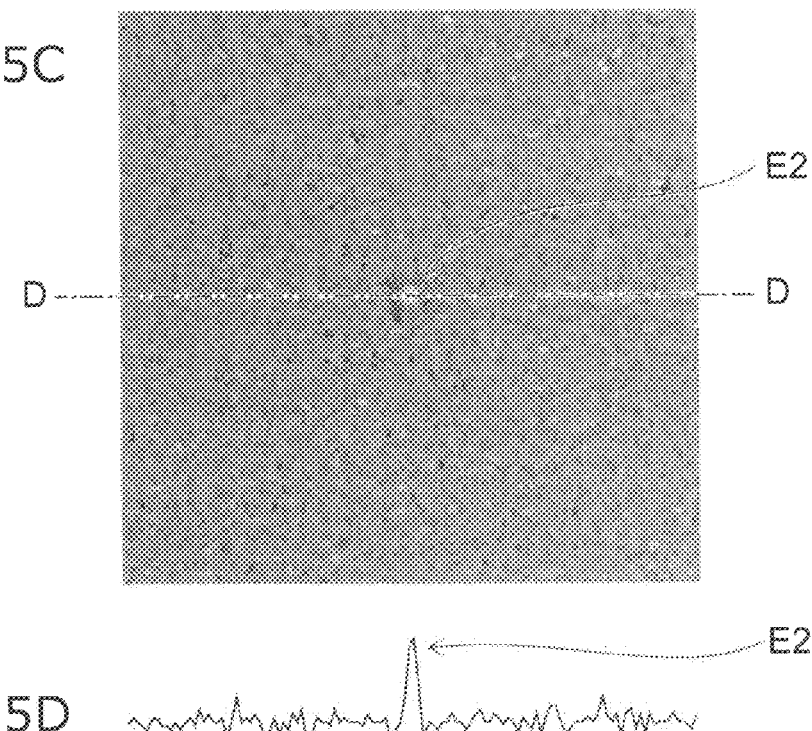
FIGS. 5C and 5D show the case where the level difference calculation section is provided.
Figure 5D:
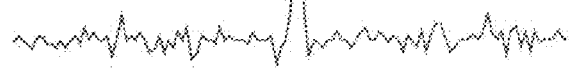

More specifically, FIGS. 5A and 5B show the case where no level difference calculation section is provided. FIGS. 5C and 5D show the case where the level difference calculation section is provided. FIG. 5B is a profile of the output level along line C-C in FIG. 5A. FIG. 5D is a profile of the output level along line D-D in FIG. 5C. E1 in FIGS. 5A and 5B, and E2 in FIGS. 5C and 5D represent defect portions.

In the case where there is a defect portion E1 as shown in FIG. 5A, the output level of the defect portion E1 is higher than the output level of the surrounding region as shown in FIG. 5B.

Also in the case where there is a defect portion E2 as shown in FIG. 5C, the output level of the defect portion E2 is higher than the output level of the surrounding region as shown in FIG. 5D.

However, FIGS. 5C and 5D show the case where the level difference calculation section 34 is provided. Thus, the average of the output level of the surrounding region 102 is subtracted. Hence, as shown in FIG. 5D, the output level of the surrounding region around the defect portion E2 is flattened. As a result, the S/N ratio in defect determination can be increased, where the output level of the defect portion E2 is denoted by S, and the maximum output level of the surrounding region is denoted by N. This enables the determination section 35 to determine a finer defect.

In the case illustrated in FIGS. 5A to 5D, the output level of the defect portion is higher (the defect portion is lighter). On the other hand, the output level of the defect portion may be lower (the defect portion may be darker). However, by providing the level difference calculation section 34, the output level of the surrounding region around the defect portion is still flattened. Hence, also in the case where the output level of the defect portion is lower, the S/N ratio in defect determination can be increased by providing the level difference calculation section 34. This enables the determination section 35 to determine a finer defect.

The logic OR calculation section 36 calculates the logic OR of the determination result of the determination section 35a and the determination result of the determination section 35b. The logic OR calculation section 36 outputs the calculation result as an inspection result for the pattern based on reflected light. That is, when at least one of the determination result of the determination section 35a and the determination result of the determination section 35b is a determination result representing the presence of a defect, an inspection result representing the presence of a defect is outputted from the logic OR calculation section 36.

Although the elements provided in the reflection inspection section 3b have been illustrated above, the elements provided in the transmission inspection section 3a can be made similar thereto. The transmission inspection section 3a receives as input the inspection data from the conversion section 26a, i.e., the inspection data based on transmitted light. Then, in a similar manner to the case of the reflection inspection section 3b described above, the presence or absence of a defect is inspected.

Although the transmission inspection section 3a and the reflection inspection section 3b are provided in the case illustrated above, it is also possible to provide only one of them. However, more appropriate inspection can be performed by providing the transmission inspection section 3a and the reflection inspection section 3b.

The foregoing refers to the case of inspecting a sub-resolution pattern. In this case, the to-be-inspected pattern may include an optically resolvable pattern. Thus, as shown in FIG. 1, an output section 30 for externally outputting the inspection data and the delay data is provided so that an inspection section, not shown, for inspecting an optically resolvable pattern can be connected to the output section 30. The inspection section for inspecting an optically resolvable pattern can be based on known techniques, and hence the description thereof is omitted.

Figure 6:
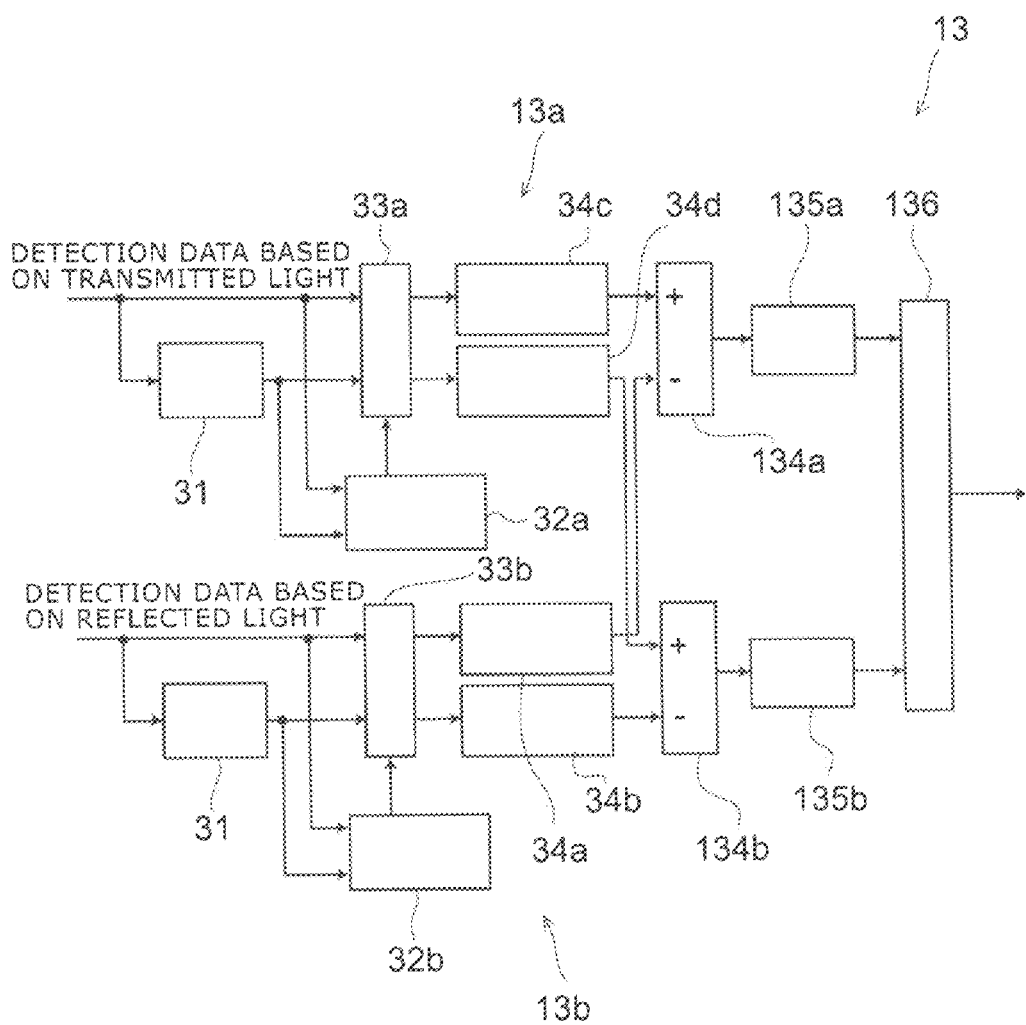
FIG. 6 is a block diagram for illustrating an inspection section according to an alternative embodiment.

FIG. 6 is a block diagram for illustrating an inspection section according to an alternative embodiment.

The pattern inspection apparatus according to the embodiment includes a inspection data creation section (second inspection data creation section) for creating inspection data (second inspection data) based on the optical image by transmitted light of a pattern formed on a to-be-inspected object 100, and a delay section (second delay section) for creating delay data (second delay data) by delaying the inspection data (e.g., the section for performing inspection by transmitted light in FIG. 1). The pattern inspection apparatus further includes a inspection data creation section (third inspection data creation section) for creating inspection data (third inspection data) based on the optical image by reflected light of the pattern formed on the to-be-inspected object 100, and a delay section (third delay section) for creating delay data (third delay data) by delaying the inspection data (e.g., the section for performing inspection by reflected light in FIG. 1).

The inspection section 13 includes a transmission inspection section 13a for performing inspection using inspection data based on transmitted light, a reflection inspection section 13b for performing inspection using inspection data based on reflected light, and a logic OR calculation section 136 (second logic OR calculation section).

The transmission inspection section 13a includes a delay section 31, a recognition section 32a (second recognition section), an extraction section 33a (second extraction section), an level difference calculation section 34c (third level difference calculation section), an level difference calculation section 34d (fourth level difference calculation section), a level difference calculation section 134a (first level difference calculation section), and a determination section 135a (third determination section).

The reflection inspection section 13b includes a delay section 31, a recognition section 32b (third recognition section), an extraction section 33b (third extraction section), an level difference calculation section 34a (fifth level difference calculation section), an level difference calculation section 34b (sixth level difference calculation section), a level difference calculation section 134b (second level difference calculation section), and a determination section 135b (fourth determination section).

The level difference calculation section 34c performs calculation based on the inspection data obtained by transmitted light. More specifically, the level difference calculation section 34c calculates the average of the output level of the surrounding region for a target pixel of the inputted inspection data. The level difference calculation section 34c further calculates the difference between the output level of a target pixel of the inputted inspection data and the average of the output level of the surrounding region for a target pixel of the inputted inspection data.

The level difference calculation section 34d performs calculation based on the delay data created from the inspection data obtained by transmitted light. More specifically, the level difference calculation section 34d calculates the average of the output level of the surrounding region for a target pixel of the inputted delay data. The level difference calculation section 34d further calculates the difference between the output level of a target pixel of the inputted delay data and the average of the output level of the surrounding region for a target pixel of the inputted delay data.

The level difference calculation section 34a performs calculation based on the inspection data obtained by reflected light. More specifically, the level difference calculation section 34a calculates the average of the output level of the surrounding region for a target pixel of the inputted inspection data. The level difference calculation section 34a further calculates the difference between the output level of a target pixel of the inputted inspection data and the average of the output level of the surrounding region for a target pixel of the inputted inspection data.

The level difference calculation section 34b performs calculation based on the delay data created from the inspection data obtained by reflected light. More specifically, the level difference calculation section 34b calculates the average of the output level of the surrounding region for a target pixel of the inputted delay data. The level difference calculation section 34b further calculates the difference between the output level of a target pixel of the inputted delay data and the average of the output level of the surrounding region for a target pixel of the inputted delay data.

The level difference calculation section 134a calculates the difference between the calculation value of the level difference calculation section 34c and the calculation value of the level difference calculation section 34a.

The level difference calculation section 134b calculates the difference between the calculation value of the level difference calculation section 34b and the calculation value of the level difference calculation section 34d.

The determination section 135a determines the presence or absence of a defect based on the input from the level difference calculation section 134a.

The determination section 135b determines the presence or absence of a defect based on the input from the level difference calculation section 134b.

The determination in the determination sections 135a, 135b can be made using a prescribed threshold.

The logic OR calculation section 136 calculates the logic OR of the determination results of the determination sections 135a, 135b. Thus, if at least one of the determination results of the determination sections 135a, 135b is a determination result representing the presence of a defect, an inspection result representing the presence of a defect is outputted from the logic OR calculation section 136.

In the aforementioned inspection section 3, the presence or absence of a defect is determined using the inspection data and delay data based on transmitted light on one hand, and the inspection data and delay data based on reflected light on the other.

In contrast, in the inspection section 13, the presence or absence of a defect is determined using the inspection data based on transmitted light and the inspection data based on reflected light on one hand, and the delay data based on transmitted light and the delay data based on reflected light on the other.

FIGS. 7A to 7F are schematic views for illustrating the operation of the inspection section.

Figure 7A:
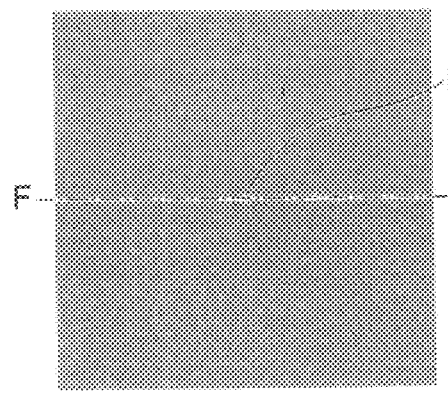
FIGS. 7A and 7B show the case of inspection using the inspection data and delay data based on transmitted light.
Figure 7C:
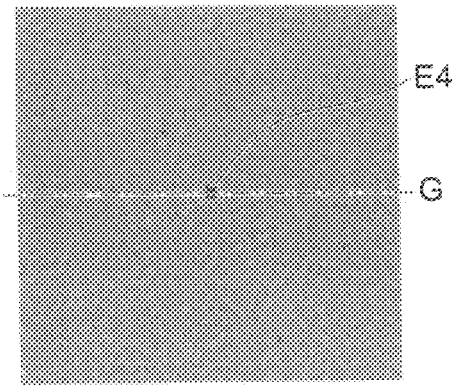
FIGS. 7C and 7D show the case of inspection using the inspection data and delay data based on reflected light.
Figure 7B:
Figure 7D:
Figure 7E:
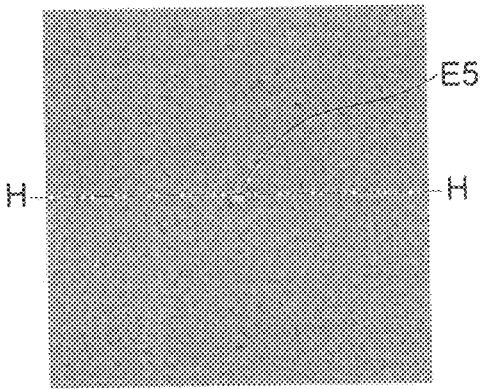
FIGS. 7E and 7F show the case of inspection using the inspection data based on transmitted light and the inspection data based on reflected light, and the delay data based on transmitted light and the delay data based on reflected light.
Figure 7F:
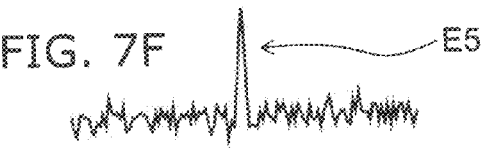

More specifically, FIGS. 7A and 7B show the case of inspection using the inspection data and delay data based on transmitted light. FIGS. 7C and 7D show the case of inspection using the inspection data and delay data based on reflected light. FIGS. 7E and 7F show the case of inspection using the inspection data based on transmitted light and the inspection data based on reflected light, and the delay data based on transmitted light and the delay data based on reflected light. FIG. 7B is a profile of the output level along line F-F in FIG. 7A. FIG. 7D is a profile of the output level along line G-G in FIG. 7C. FIG. 7F is a profile of the output level along line H-H in FIG. 7E. E3 in FIGS. 7A and 7B, E4 in FIGS. 7C and 7D, and E5 in FIGS. 7E and 7F represent defect portions.

That is, FIGS. 7A to 7D show the case of inspection by the inspection section 3, and FIGS. 7E and 7F show the case of inspection by the inspection section 13.

In the case of inspection by the inspection section 3, the polarity is inverted between transmitted light and reflected light. Hence, one of them may result in a defect portion E3 with high output level (a defect portion being light), whereas the other may result in a defect portion E4 with low output level (a defect portion being dark).

Thus, in the case of inspection by the inspection section 13, the defect portion is enhanced by calculating the difference between the data based on transmitted light and the data based on reflected light (summing them with the polarity of one of them inverted).

That is, the output level of the defect portion is the sum of the output level of the defect portion based on the transmitted light and the output level of the defect portion based on the polarity-inverted reflected light.

Here, the output level of the surrounding region (the output level of noise components) based on transmitted light and the output level of the surrounding region (the output level of noise components) based on reflected light are independent.

Thus, in the difference calculated between the data based on transmitted light and the data based on reflected light, the output level of the surrounding region is the square sum of the output level of the surrounding region based on transmitted light and the output level of the surrounding region based on reflected light.

For instance, the output level of the defect portion based on transmitted light is denoted by S. The output level of the defect portion based on reflected light is denoted by −S. The output levels of the surrounding region based on transmitted light and based on reflected light are both denoted by N. Then, the output level of the defect portion is 2S, and the output level of the surrounding region is 1.4N.

Thus, the S/N ratio in defect determination can be further increased. Hence, an even finer defect can be determined.

According to the embodiment, sufficient inspection sensitivity can be achieved even for an optically unresolvable pattern.

Furthermore, by providing the level difference calculation section, the output level of the surrounding region can be flattened. Thus, the S/N ratio in defect determination can be increased. Hence, a finer defect can be determined.

Furthermore, the defect portion can be enhanced by calculating the difference between the data based on transmitted light and the data based on reflected light (summing them with the polarity of one of them inverted). Thus, the S/N ratio in defect determination can be further increased. Hence, an even finer defect can be determined.

[Second Embodiment]

Figure 8:
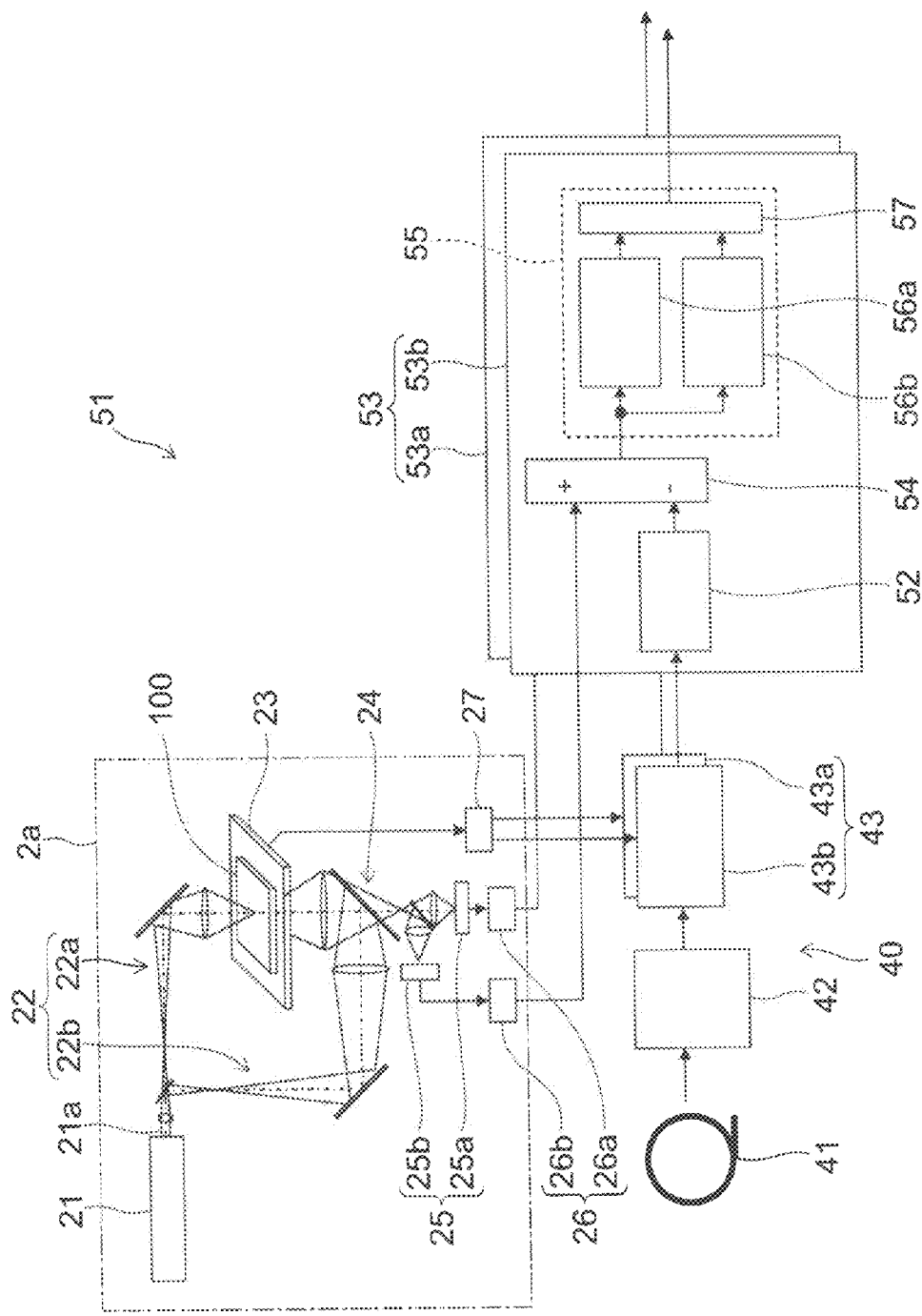
FIG. 8 is a block diagram for illustrating a pattern inspection apparatus according to a second embodiment.

FIG. 8 is a block diagram for illustrating a pattern inspection apparatus according to a second embodiment. As an example, FIG. 8 illustrates a pattern inspection apparatus for inspecting a pattern using the die-to-database method.

As shown in FIG. 8, the pattern inspection apparatus 51 includes a inspection data creation section 2a, a reference data creation section 40 (first reference data creation section), and an inspection section 53.

The inspection data creation section 2a includes a light source 21, an illumination optical system 22, a mounting section 23, an imaging optical system 24, a detection section 25, a conversion section 26, and a position detection section 27.

The position detection section 27 obtains position information of the mounting section 23 and provides the position information to the data creation section 43 described later. Examples of the position detection section 27 can include a laser interferometer and a linear encoder. However, the position detection section 27 is not limited thereto, but a device capable of converting the position information of the mounting section 23 to an electrical signal can be suitably selected.

The reference data creation section 40 includes a data storage section 41, a data expansion section 42, and a data creation section 43.

The reference data creation section 40 creates reference data (first reference data) based on e.g. design data stored in the data storage section 41. That is, the reference data creation section 40 creates reference data concerning a pattern formed on a to-be-inspected object 100.

The data storage section 41 stores e.g. delineation data used to form a pattern, or design data to be converted to the delineation data.

The data expansion section 42 expands e.g. design data provided from the data storage section 41 into a bit pattern.

The data creation section 43 creates reference data by image interpretation of the data expanded into the bit pattern. Here, the reference data is created in accordance with the resolution of the inspection data.

The data creation section 43 extracts, from the reference data, a target portion of the reference data based on the position information of the mounting section 23 provided from the position detection section 27, and outputs the target portion of the reference data. More specifically, position information concerning the inspection region of the to-be-inspected object 100 held on the mounting section 23 is obtained from the position information of the mounting section 23. In accordance with the position of the inspection region (the position of data captured by the detection section 25), a target portion of the reference data is extracted from the reference data and outputted.

The data creation section 43 includes a data creation section 43a for providing reference data to the transmission inspection section 53a and a data creation section 43b for providing reference data to the reflection inspection section 53b, described later. Here, the data creation section 43a and the data creation section 43b can be made similar.

The inspection section 53 includes a transmission inspection section 53a for performing inspection using inspection data based on transmitted light, and a reflection inspection section 53b for performing inspection using inspection data based on reflected light.

The transmission inspection section 53a and the reflection inspection section 53b include a gradation conversion section 52 (first gradation conversion section), a level difference calculation section 54 (third level difference calculation section), and a determination section 55 (fifth determination section).

The elements provided in the transmission inspection section 53a can be made similar to the elements provided in the reflection inspection section 53b. Thus, by way of example, the elements provided in the reflection inspection section 53b are illustrated.

As described above, reference data is created by expanding e.g. design data into a bit pattern. Here, for each target pixel, the proportion occupied in the expanded pattern data is calculated, and reference data is created based on the proportion. For instance, pixels occupying a proportion of 0%, 50%, and 100% in the pattern data are converted to numerical values such as 0, 50, and 100, respectively, and thus reference data is created.

For an optically resolvable pattern, the reference data created in such a method has an output level corresponding to the proportion occupied in the pattern data, and hence corresponds to the output level of the detection section 25.

However, for a sub-resolution pattern, transmittance and reflectance are changed due to e.g. the shape condition of the sub-resolution pattern. Hence, the reference data may fail to correspond to the output level of the detection section 25.

Thus, in the embodiment, the output level is converted by the gradation conversion section 52 so that the output level of the reference data corresponds to the output level of the detection section 25.

The gradation conversion section 52 converts the output level so that the output level of the reference data corresponds to the output level of the detection section 25. Here, the output level can be converted using a predetermined gradation conversion table. The gradation conversion table can be previously determined by e.g. experiment or simulation.

The level difference calculation section 54 calculates the difference between the inspection data from the conversion section 26b and the reference data whose output level has been converted by the gradation conversion section 52.

The determination section 55 includes a determination section 56a for making a determination on the input data from the level difference calculation section 54 using the threshold of the lower bound, a determination section 56b for making a determination on the input data from the level difference calculation section 54 using the threshold of the upper bound, and a logic OR calculation section 57.

The logic OR calculation section 57 calculates the logic OR of the determination results of the determination sections 56a, 56b. Thus, if at least one of the determination results of the determination sections 56a, 56b is a determination result representing the presence of a defect, the logic OR calculation section 57 outputs an inspection result representing the presence of a defect.

FIG. 9 is a schematic view for illustrating the operation of the reflection inspection section 53b.

In FIG. 9, data P1 represents image data in the inspection data. Data P2 represents image data in the reference data. Data P3 represents image data converted by the gradation conversion section. The diagrams depicted below the data P1-P3 are profiles of the output level along the horizontal direction of the respective image data.

In the image data, A, A1, and A2 represent sub-resolution patterns, and B, B1, and B2 represent optically resolvable patterns.

The graph J in FIG. 9 is a graphical representation of the gradation conversion table. The graph 3 shows that the output level is converted in the region indicated by the portion K in the graph J. As an example, the graph 3 illustrates the case of increasing the output level in the region indicated by the portion K. Here, the gradation conversion table is not limited to that illustrated in the graph J, but can be suitably modified.

As described above, transmittance and reflectance are changed due to e.g. the shape condition of the sub-resolution pattern. Hence, the reference data may fail to correspond to the output level of the detection section 25. This may cause a difference between the data P1 and the data P2.

Thus, the output level of the data P2 is converted by the gradation conversion section 52 so that the output level of the converted data P3 corresponds to the output level of the data P1.

Then, the difference between the data P1 and the data P3 is calculated by the level difference calculation section 54. The data calculated by the level difference calculation section 54 is inputted to the determination sections 56a, 56b, and subjected to a determination using the threshold of the lower bound and the threshold of the upper bound, respectively. The logic OR of the determination results of the determination sections 56a, 56b is calculated in the logic OR calculation section 57. If at least one of the determination results of the determination sections 56a, 56b is a determination result representing the presence of a defect, an inspection result representing the presence of a defect is outputted.

Although the elements provided in the reflection inspection section 53b have been illustrated above, the elements provided in the transmission inspection section 53a can be made similar thereto. The transmission inspection section 53a receives as input the inspection data from the conversion section 26a, i.e., the inspection data based on transmitted light. Then, in a similar manner to the case of the reflection inspection section 53b described above, the presence or absence of a defect is inspected.

Although the transmission inspection section 53a and the reflection inspection section 53b are provided in the case illustrated above, it is also possible to provide only one of them. However, more appropriate inspection can be performed by providing the transmission inspection section 53a and the reflection inspection section 53b.

FIG. 10 is a block diagram for illustrating an inspection section according to an alternative embodiment.

As shown in FIG. 10, the inspection section 153 includes a gradation conversion section 52, a recognition section 132 (fourth recognition section), an extraction section 133 (fourth extraction section), a level difference calculation section 54, and a determination section 55. Here, the inspection section 153 includes a transmission inspection section 153a for performing inspection using inspection data based on transmitted light, and a reflection inspection section 153b for performing inspection using inspection data based on reflected light. However, in both of them, the configuration itself can be made similar.

The recognition section 132 recognizes whether or not the inputted reference data is data concerning the image of a sub-resolution pattern. Here, the recognition section 132 can be made similar to the aforementioned recognition section 32, and hence the description of its configuration and operation is omitted.

In response to input of the "recognition flag" from the recognition section 132, the extraction section 133 outputs the corresponding inspection data and the reference data converted by the gradation conversion section 52 toward the level difference calculation section 54. That is, the reference data recognized as data of a sub-resolution pattern by the recognition section 132, and the corresponding inspection data are outputted toward the level difference calculation section 54. Here, the extraction section 133 can be made similar to the aforementioned extraction section 33, and hence the description of its configuration and operation is omitted.

In this manner, it is possible to inspect only sub-resolution patterns.

In this case, the to-be-inspected pattern may include an optically resolvable pattern. Thus, as shown in FIG. 10, an output section 30a for externally outputting the inspection data and the reference data converted by the gradation conversion section 52 is provided so that an inspection section, not shown, for inspecting an optically resolvable pattern can be connected to the output section 30a. The inspection section for inspecting an optically resolvable pattern can be based on known techniques, and hence the description thereof is omitted.

According to the embodiment, sufficient inspection sensitivity can be achieved even for an optically unresolvable pattern.

Furthermore, the gradation conversion section 52 is provided so that the output level of the reference data can correspond to the output level of the detection section 25. Thus, the inspection accuracy can be improved, and a finer defect can be determined.

Furthermore, by providing the recognition section 132, an optically unresolvable pattern, which is conventionally difficult to inspect, can be preferentially inspected.

[Third Embodiment]

Figure 11:
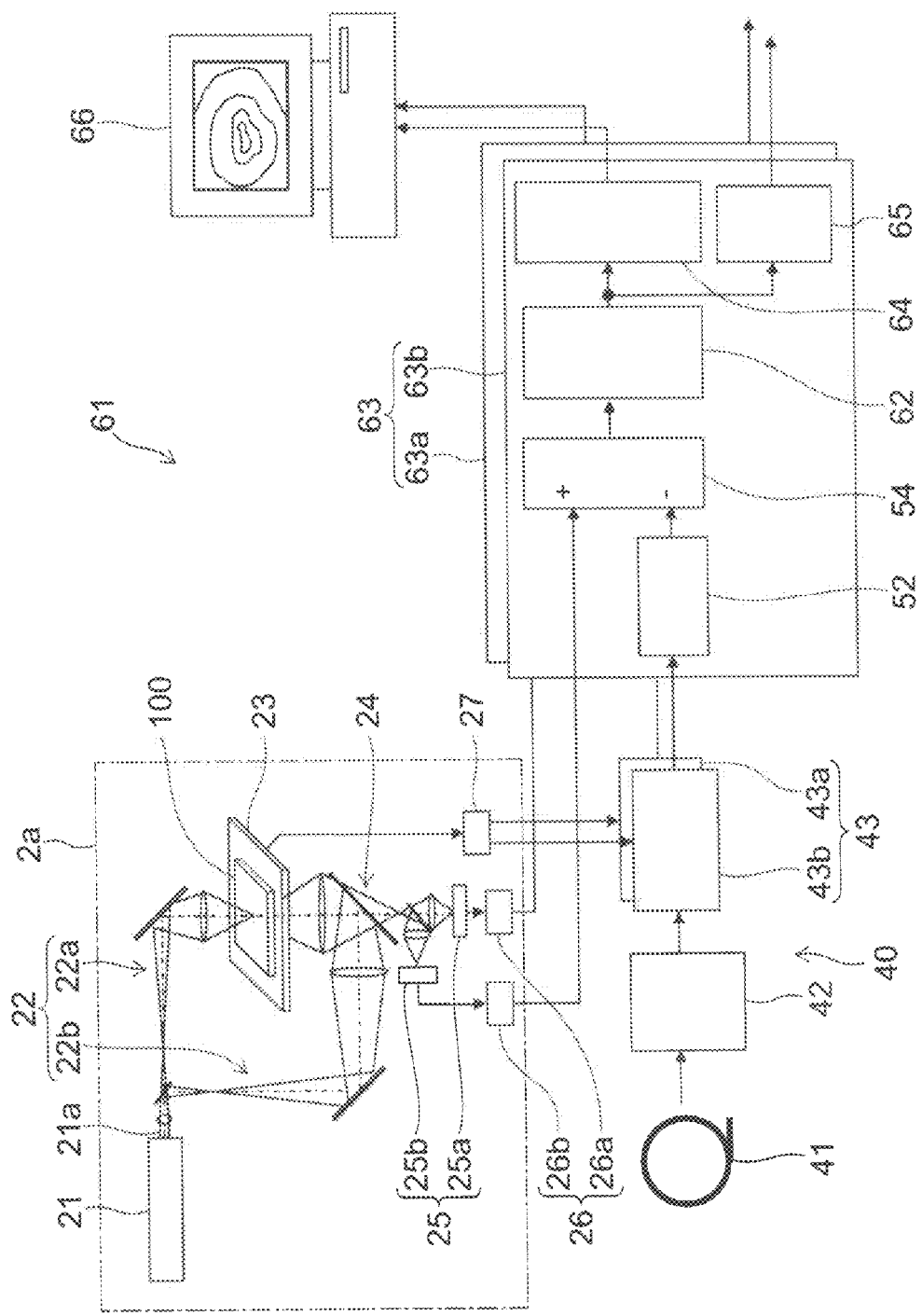
FIG. 11 is a block diagram for illustrating a pattern inspection apparatus according to a third embodiment.

FIG. 11 is a block diagram for illustrating a pattern inspection apparatus according to a third embodiment. As an example, FIG. 11 illustrates a pattern inspection apparatus for inspecting a pattern using the die-to-database method.

As described later, pattern transmittance and reflectance are changed due to e.g. the shape condition of the pattern such as the ratio of the line portion to the space portion and the height dimension of the pattern, the proportion occupied by the thin layer on the surface (such as chromium (Cr) layer), and the thickness of the layer.

Thus, in the embodiment, the degree of change of transmittance and reflectance of the sub-resolution pattern is also measured to inspect the change of the pattern line width and the change of the process condition during pattern formation.

The influence of e.g. the shape condition of the pattern on transmittance and reflectance will be described later.

As shown in FIG. 11, the pattern inspection apparatus 51 includes a inspection data creation section 2a, a reference data creation section 40, and an inspection section 63.

The inspection data creation section 2a includes a light source 21, an illumination optical system 22, a mounting section 23, an imaging optical system 24, a detection section 25, a conversion section 26, and a position detection section 27.

The reference data creation section 40 includes a data storage section 41, a data expansion section 42, and a data creation section 43.

The inspection section 63 includes a transmission inspection section 63a for performing inspection using inspection data based on transmitted light, and a reflection inspection section 63b for performing inspection using inspection data based on reflected light.

The elements provided in the transmission inspection section 63a can be made similar to the elements provided in the reflection inspection section 63b. Thus, by way of example, the elements provided in the reflection inspection section 63b are illustrated.

The reflection inspection section 63b includes a gradation conversion section 52, a level difference calculation section 54, an average level difference calculation section 62, a distribution collect section 64, a determination section 65, and a display section 66.

The average level difference calculation section 62 calculates the average of input data from the level difference calculation section 54. Here, the average in a certain predetermined region (e.g., a region of N pixels×N pixels in the inspection data) is calculated.

The distribution collect section 64 collects the averages calculated by the average level difference calculation section 62 over the entire inspection region of the to-be-inspected object 100.

By thus aggregating data over the entire inspection region of the to-be-inspected object 100, the degree of change of reflectance can be measured. In the transmission inspection section 63a, the degree of change of transmittance can be measured.

Then, by measuring the degree of change of transmittance and reflectance of the sub-resolution pattern, the change of the pattern line width and the change of the process condition during pattern formation can be inspected. Furthermore, abnormality factors in the manufacturing process, for instance, can also be found.

Furthermore, for instance, the change of the process condition in the writing process and etching process during pattern formation can be measured. Thus, the condition for reducing the change can be fed back to the writing process and etching process during pattern formation.

In the case where such a patterned object is used to manufacture another product, the changed pattern line width, for instance, can be fed forward to the downstream process to increase the yield of the product. For instance, in the case where the to-be-inspected object 100 is a photomask, the changed pattern line width, for instance, can be fed forward to the lithography process to increase the yield of e.g. semiconductor devices.

The determination section 65 makes a determination on the average calculated by the average level difference calculation section 62 using e.g. two thresholds of an upper bound and a lower bound. The determination section 65 can determine the portion beyond the thresholds to be a defect portion. The configuration of the determination section 65 can be made similar to that of the aforementioned determination section 55, and hence the description thereof is omitted.

The display section 66 displays information collected by the distribution collect section 64.

For instance, the degree of change of reflectance (in the case of the transmission inspection section 63*a*, the degree of change of transmittance) provided from the distribution collect section 64 can be displayed as a two-dimensional map using contours and color bars.

Although the elements provided in the reflection inspection section 63*b* have been illustrated above, the elements provided in the transmission inspection section 63*a* can be made similar thereto. The transmission inspection section 63*a* receives as input the inspection data from the conversion section 26*a*, i.e., the inspection data based on transmitted light. Then, in a similar manner to the case of the reflection inspection section 63*b* described above, the presence or absence of a defect is inspected.

Although the transmission inspection section 63*a* and the reflection inspection section 63*b* are provided in the case illustrated above, it is also possible to provide only one of them. However, more appropriate inspection can be performed by providing the transmission inspection section 63*a* and the reflection inspection section 63*b*.

Figure 12:
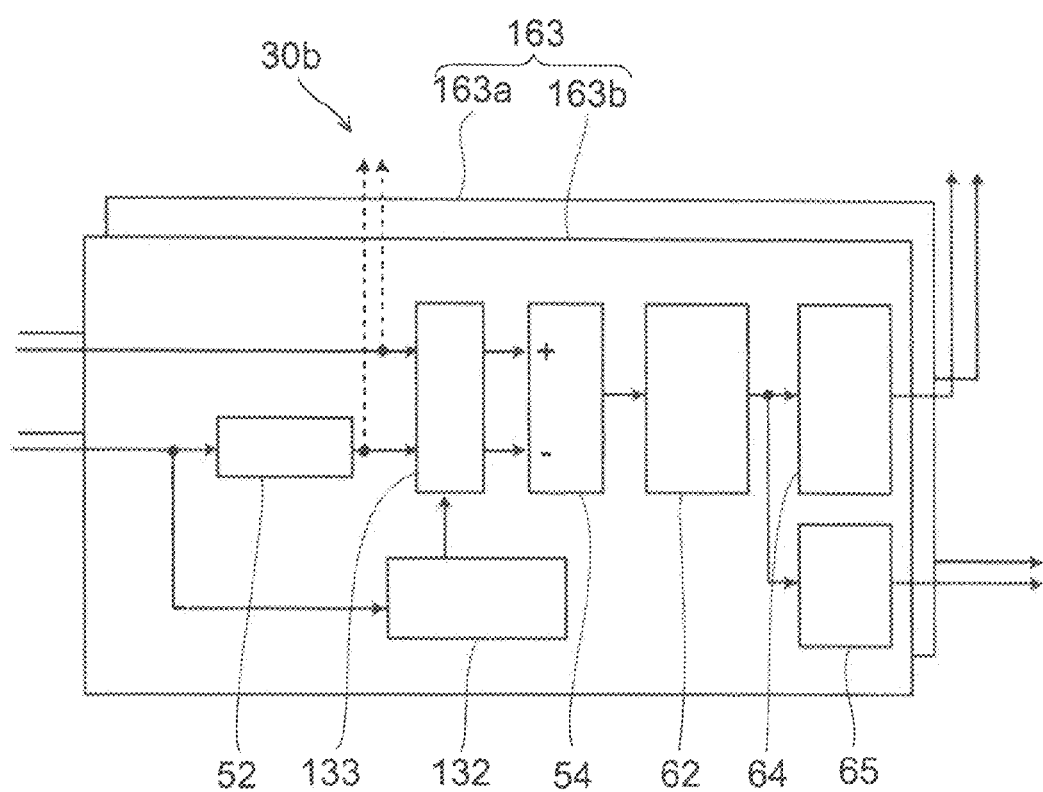
FIG. 12 is a block diagram for illustrating an inspection section according to an alternative embodiment.

FIG. 12 is a block diagram for illustrating an inspection section according to an alternative embodiment.

As shown in FIG. 12, the inspection section 163 includes a gradation conversion section 52, a recognition section 132, an extraction section 133, a level difference calculation section 54, an average level difference calculation section 62, a distribution collect section 64, and a determination section 65.

The inspection section 163 includes a transmission inspection section 163*a* for performing inspection using inspection data based on transmitted light, and a reflection inspection section 163*b* for performing inspection using inspection data based on reflected light. However, in both of them, the configuration itself can be made similar.

The elements themselves provided in the inspection section 163 can be made similar to those described above, and hence the description thereof is omitted.

Like that illustrated in FIG. 10, the inspection section 163 includes a recognition section 132 and an extraction section 133. Thus, the inspection section 163 can inspect only sub-resolution patterns.

In this case, the to-be-inspected pattern may include an optically resolvable pattern. Thus, as shown in FIG. 12, an output section 30*b* for externally outputting the inspection data and the reference data converted by the gradation conversion section 52 is provided so that an inspection section, not shown, for inspecting an optically resolvable pattern can be connected to the output section 30*b*. The inspection section for inspecting an optically resolvable pattern can be based on known techniques, and hence the description thereof is omitted.

According to the embodiment, sufficient inspection sensitivity can be achieved even for an optically unresolvable pattern.

Furthermore, the average level difference calculation section and the distribution collect section are provided so that the degree of change of transmittance and reflectance can be measured. Thus, it is possible to inspect the shape condition of the pattern such as the ratio of the line portion to the space portion and the height dimension of the pattern, the proportion occupied by the thin layer on the surface, and the thickness of the layer (such as the change of the pattern line width and the change of the process condition during pattern formation). Furthermore, abnormality factors in the manufacturing process, for instance, can also be found. Furthermore, the condition for reducing the change can be fed back to the process for forming the pattern. Furthermore, the changed pattern line width, for instance, can be fed forward to the downstream process. Thus, the yield of products can be increased.

Furthermore, the gradation conversion section 52 is provided so that the output level of the reference data can correspond to the output level of the detection section 25. Thus, the inspection accuracy can be improved, and a finer defect can be determined.

Furthermore, by providing the recognition section 132, an optically unresolvable pattern, which is conventionally difficult to inspect, can be preferentially inspected.

[Fourth Embodiment]

Figure 13A:
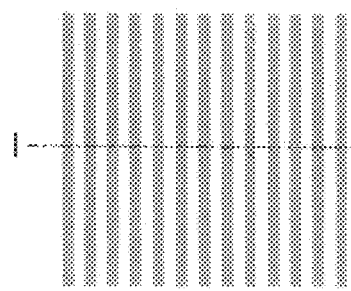
FIG. 13A is a schematic enlarged view of a striped pattern having a prescribed repetition pitch.
Figure 13C:
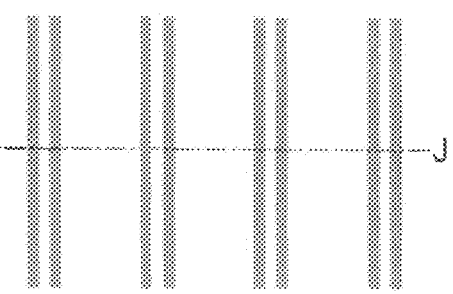
FIG. 13C is also a schematic enlarged view of a striped pattern having a prescribed repetition pitch.
Figure 13B:
FIG. 13B is a profile of the output level along line I-I in FIG. 13A.
Figure 13D:
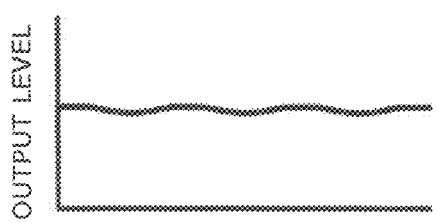
FIG. 13D is a profile of the output level along line J-J in FIG. 13C.
Figure 13E:
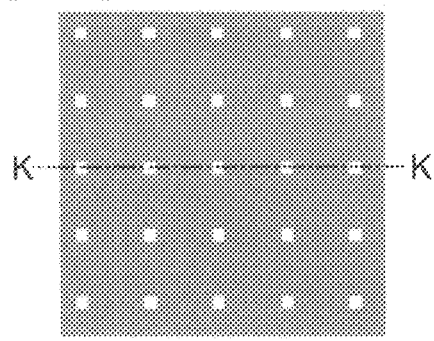
FIG. 13E is a schematic enlarged view of a dotted pattern having a prescribed repetition pitch.
Figure 13F:
FIG. 13F is a profile of the output level along line K-K in FIG. 13E.

FIGS. 13A to 13F are schematic views for illustrating the relationship between a sub-resolution pattern having a prescribed repetition pitch and the output level of inspection data. More specifically, FIG. 13A is a schematic enlarged view of a striped pattern having a prescribed repetition pitch. FIG. 13B is a profile of the output level along line I-I in FIG. 13A. FIG. 13C is also a schematic enlarged view of a striped pattern having a prescribed repetition pitch. FIG. 13D is a profile of the output level along line J-J in FIG. 13C. FIG. 13E is a schematic enlarged view of a dotted pattern having a prescribed repetition pitch. FIG. 13F is a profile of the output level along line K-K in FIG. 13E.

In a sub-resolution pattern, the pattern itself cannot be optically resolved. However, for instance, in the case where the sub-resolution pattern is arranged in a prescribed pitch as shown in FIGS. 13A, 13C, and 13E, the output level of inspection data changes at a prescribed repetition pitch as shown in FIGS. 13B, 13D, and 13F.

Hence, by measuring the repetition pitch and the degree of change of the output level of inspection data, the geometry of the sub-resolution pattern (such as the shape and pitch dimension of the pattern) can be identified.

Thus, in the embodiment, the sub-resolution pattern is extracted, and a pattern having a specific repetition pitch is detected from the extracted sub-resolution pattern by correlation calculation.

Then, based on the detected pattern having a specific repetition pitch, the presence or absence of a defect is determined.

Figure 14:
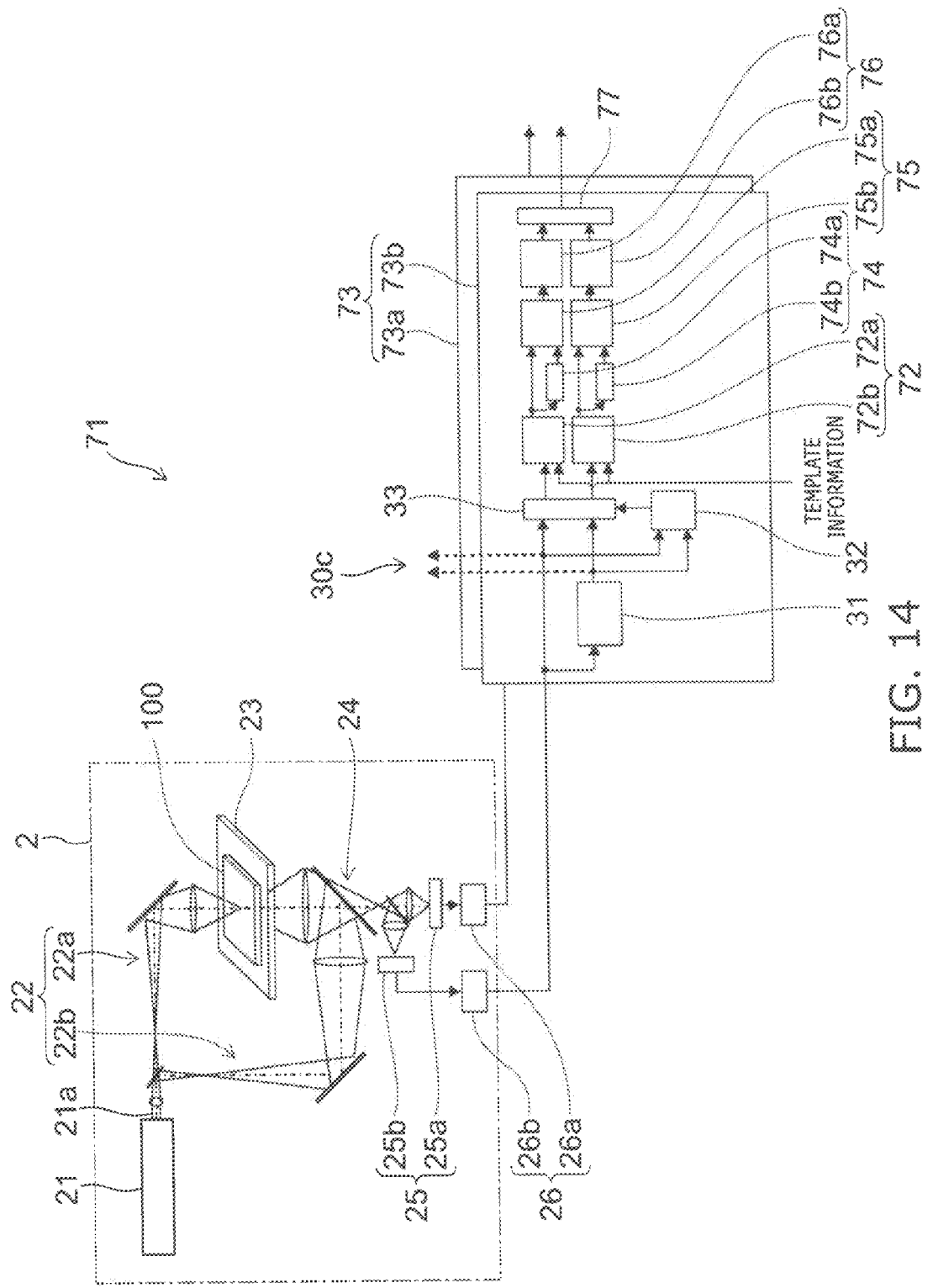
FIG. 14 is a block diagram for illustrating a pattern inspection apparatus according to a fourth embodiment.

FIG. 14 is a block diagram for illustrating a pattern inspection apparatus according to a fourth embodiment. As an example, FIG. 14 illustrates a pattern inspection apparatus for inspecting a pattern using the die-to-die method.

As shown in FIG. 14, the pattern inspection apparatus 71 includes a inspection data creation section 2 and an inspection section 73.

The inspection section 73 includes a transmission inspection section 73*a* for performing inspection using inspection data based on transmitted light, and a reflection inspection section 73*b* for performing inspection using inspection data based on reflected light.

The elements provided in the transmission inspection section 73*a* can be made similar to the elements provided in the reflection inspection section 73*b*. Thus, by way of example, the elements provided in the reflection inspection section 73*b* are illustrated.

The reflection inspection section 73*b* includes a delay section 31, a recognition section 32, an extraction section 33, a pattern extraction section 72, a pattern delay section 74, a comparison section 75, a determination section 76, and a logic OR calculation section 77 (third logic OR calculation section).

Figure 15:
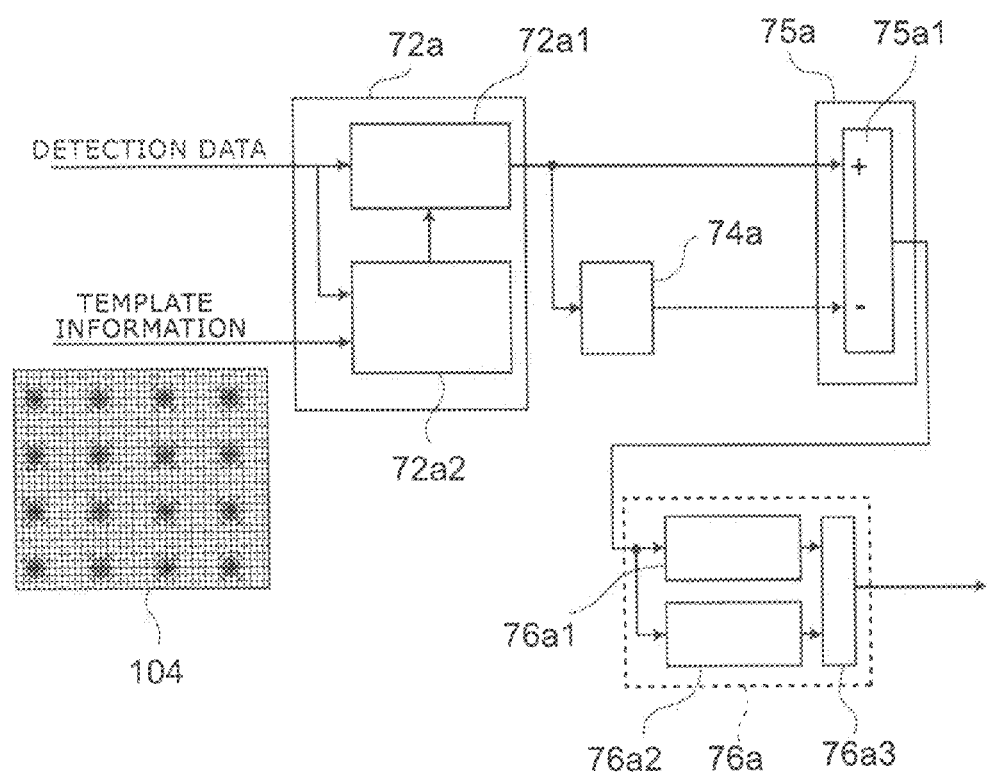
FIG. 15 is a block diagram for illustrating the pattern extraction section, the pattern delay section, the comparison section, and the determination section.

FIG. 15 is a block diagram for illustrating the pattern extraction section, the pattern delay section, the comparison section, and the determination section in FIG. 14.

On the inspection data input side, a pattern extraction section 72a (first pattern extraction section), a pattern delay section 74a (fourth delay section), a comparison section 75a (level difference calculation section 75a1 (fourth level difference calculation section)), and a determination section 76a (seventh determination section) are provided.

On the delay data input side, a pattern extraction section 72b (second pattern extraction section), a pattern delay section 74b (fifth delay section), a comparison section 75b (level difference calculation section (fifth level difference calculation section)), and a determination section 76b (eighth determination section) are provided.

Here, the elements provided on the inspection data input side can be made similar to the elements provided on the delay data input side. Thus, by way of example, the elements provided on the inspection data input side are illustrated.

The pattern extraction section 72a includes a pattern extraction section 72a1 and a correlation calculation section 72a2.

The pattern extraction section 72a1 receives as input the inspection data through the extraction section 33. More specifically, like that described above, the inspection data recognized in the recognition section 32 as data concerning the image of a sub-resolution pattern is inputted to the pattern extraction section 72a1.

On the other hand, the correlation calculation section 72a2 receives as input the inspection data through the extraction section 33, and template information 104. More specifically, the inspection data recognized in the recognition section 32 as data concerning the image of a sub-resolution pattern, and the template information 104 are inputted to the correlation calculation section 72a2.

The correlation calculation section 72a2 performs correlation calculation (pattern matching) of the inputted sub-resolution pattern and the pattern having a specific repetition pitch included in the template information 104. If matched, the correlation calculation section 72a2 outputs a "template matching result". The "template matching result" is outputted as a "valid flag" toward the pattern extraction section 72a1.

The pattern extraction section 72a1 extracts the data of the pattern matched in the correlation calculation section 72a2 from the inspection data.

The pattern delay section 74a receives as input the data concerning the pattern extracted by the pattern extraction section 72a1.

The pattern delay section 74a inserts a certain time delay in the transfer of the inputted data to create comparison data (first comparison data) for comparison with data subsequently outputted from the pattern extraction section 72a1. On the other hand, the pattern delay section 74b provided on the delay data input side inserts a certain time delay in the transfer of the inputted data to create comparison data (second comparison data) for comparison with data subsequently outputted from the pattern extraction section provided in the pattern extraction section 72b. The pattern delay section 74a, 74b then outputs the created data toward the comparison section 75a, 75b, respectively.

The comparison section 75a includes a level difference calculation section 75a1 (fourth level difference calculation section).

The level difference calculation section 75a1 calculates the difference between the data inputted from the pattern extraction section 72a1 and the data inputted from the delay section 74a. Then, the level difference calculation section 75a1 outputs the calculated data toward the determination section 76a.

The determination section 76a includes determination sections 76a1, 76a2 and a logic OR calculation section 76a3.

The determination sections 76a1, 76a2 make a determination on the inputted data using two thresholds of an upper bound and a lower bound. For instance, the determination section 76a1 can make a determination using the threshold of the lower bound, and the determination section 76a2 can make a determination using the threshold of the upper bound.

The logic OR calculation section 76a3 calculates the logic OR of the determination result of the determination section 76a1 and the determination result of the determination section 76a2. Thus, if at least one of the determination result of the determination section 76a1 and the determination result of the determination section 76a2 is a determination result representing the presence of a defect, the logic OR calculation section 76a3 outputs a determination result representing the presence of a defect toward the logic OR calculation section 77.

The logic OR calculation section 77 receives as input the determination result from the determination section 76a and the determination result from the determination section 76b. That is, similar calculation is performed on the delay data input side, and a determination result concerning the presence or absence of a defect is inputted from the determination section 76b to the logic OR calculation section 77.

The logic OR calculation section 77 calculates the logic OR of the determination result of the determination section 76a and the determination result of the determination section 76b. Thus, if at least one of the determination result of the determination section 76a and the determination result of the determination section 76b is a determination result representing the presence of a defect, an inspection result representing the presence of a defect is outputted from the logic OR calculation section 77.

Although the transmission inspection section 73a and the reflection inspection section 73b are provided in the case illustrated above, it is also possible to provide only one of them. However, more appropriate inspection can be performed by providing the transmission inspection section 73a and the reflection inspection section 73b.

The correlation calculation (pattern matching) in the correlation calculation section 72a2 described above refers to the case of using a fixed template. However, it is also possible to use a variable template which can arbitrarily specify the matching region.

Figure 16:
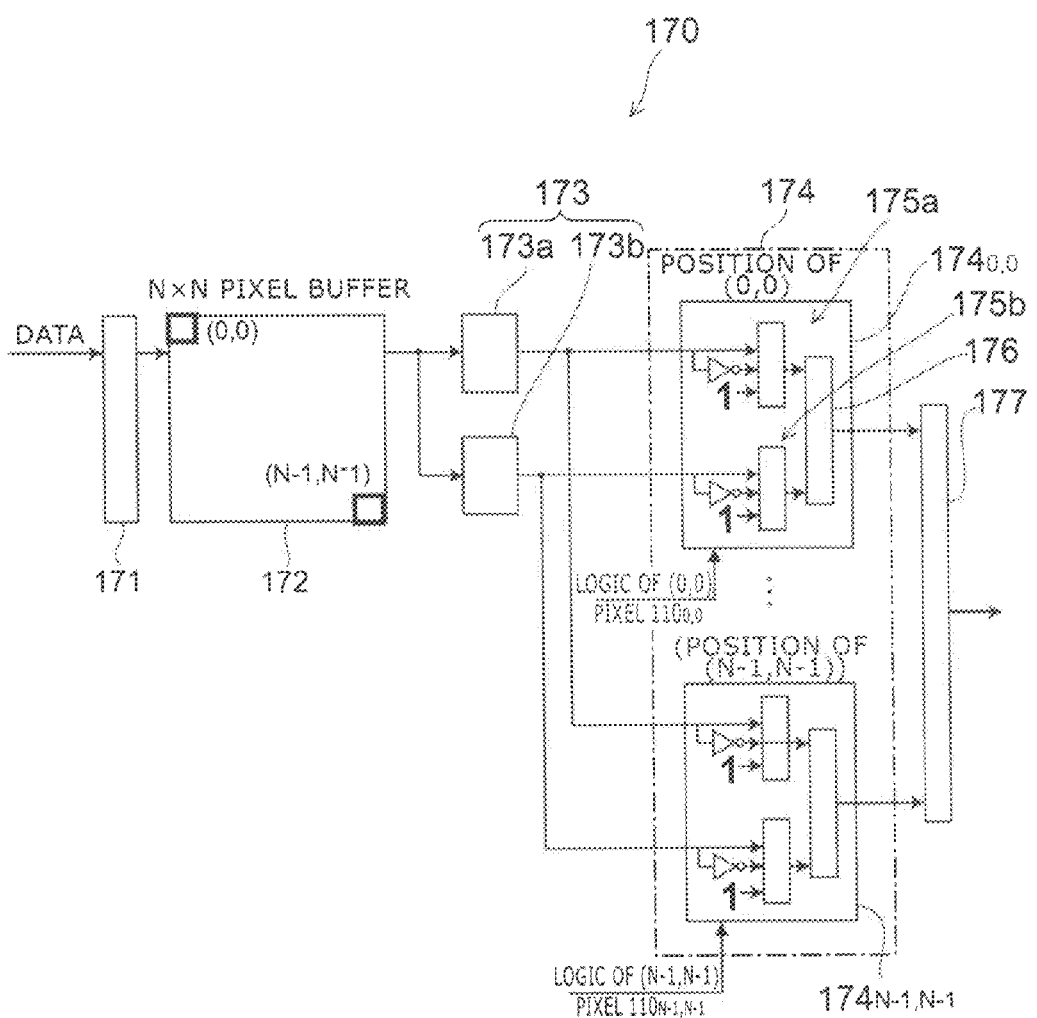
FIG. 16 is a block diagram for illustrating a variable template.

FIG. 16 is a block diagram for illustrating a variable template.

As shown in FIG. 16, the variable template 170 includes a delay section 171, a buffer section 172, a binarization section 173, a matching section 174, and a logic AND calculation section 177.

The delay section 171 inserts a certain time delay in the transfer of the inputted data (e.g., inspection data) without changing the waveform of its electrical signal.

The buffer section 172 accumulates the data inputted through the delay section 171 as data of N×N pixels.

The binarization section 173 includes conversion sections 173a, 173b. The conversion sections 173a, 173b perform binarization using different thresholds (e.g., threshold X1 and threshold X2).

The data of N×N pixels accumulated in the buffer section 172 is binarized using the different thresholds in the binarization section 173. The binarized data is provided to pixel matching sections $174_{0,0}$-$174_{N-1,N-1}$ respectively corresponding to the N×N pixels. The thresholds can be arbitrarily changed.

The matching section 174 includes pixel matching sections $174_{0,0}$-$174_{N-1,N-1}$ respectively corresponding to the N×N pixels. Each matching section $174_{0,0}$-$174_{N-1,N-1}$ includes logic calculation sections 175a, 175b and a logic AND calculation section 176.

The logic in the logic calculation sections 175a, 175b can be arbitrarily specified. More specifically, by arbitrarily specifying the logic in the logic calculation sections 175a, 175b, a variable template is configured in which the logic in the pixel constituting the template can be arbitrarily specified.

For instance, in the logic calculation section 175a, at least one of "corresponding pixel value>threshold X1, corresponding pixel value≤threshold X1, and calculation unnecessary" is to be selected and specified. In the logic calculation section 175b, at least one of "corresponding pixel value>threshold X2, corresponding pixel value≤threshold X2, and calculation unnecessary" is to be selected and specified. Thus, the data provided from the binarization section 173 is determined by the specified logic.

Here, "calculation unnecessary" can be selected and specified in the case where the corresponding pixel value is obvious. For instance, the pixel located in the hole portion (transmitting portion) of a hole pattern is obviously "light". In such cases, by selecting and specifying "1" in the figure, the corresponding pixel can always be determined as "ON (light)".

The logic AND calculation section 176 calculates the logic AND of the determination results outputted from the logic calculation sections 175a, 175b to output a matching result in the corresponding pixel.

The logic AND calculation section 177 further calculates the logic AND of the matching results of the logic AND calculation sections 176 in the respective pixel matching sections $174_{0,0}$-$174_{N-1,N-1}$. If matched, the logic AND calculation section 177 outputs a "template matching result". The "template matching result" is outputted as a "valid flag" toward the pattern extraction section 72a1.

Thus, in accordance with the logic specification of the specified template, the logic AND of the matching results of all the N×N pixels can be calculated. This enables template matching in an arbitrary logic specification. If template matching can be performed in an arbitrary logic specification, a template conforming to e.g. the shape of the pattern subjected to characteristics detection can be easily selected from e.g. "detection recipes".

The binarization section 173 is not limited to binarization using two different thresholds, but may perform binarization using three or more thresholds. In this case, if the number of logic calculation sections in the matching section is increased with the number of thresholds, template matching can be performed in a more arbitrary condition also in terms of the brightness level.

The foregoing refers to the case of inspecting a sub-resolution pattern. In this case, the to-be-inspected pattern may include an optically resolvable pattern. Thus, as shown in FIG. 14, an output section 30c for externally outputting the inspection data and the delay data is provided so that an inspection section, not shown, for inspecting an optically resolvable pattern can be connected to the output section 30c. The inspection section for inspecting an optically resolvable pattern can be based on known techniques, and hence the description thereof is omitted.

According to the embodiment, sufficient inspection sensitivity can be achieved even for an optically unresolvable pattern.

Furthermore, by the correlation calculation section, a pattern having a specific repetition pitch can be detected from the inputted sub-resolution pattern. Based on the detected pattern having a specific repetition pitch, the presence or absence of a defect can be determined.

Here, by comparison between the detected patterns having specific repetition pitches, comparison inspection can be performed while mutually canceling the variation of the output level of the patterns.

Thus, in a sub-resolution pattern having a specific repetition pitch, a finer defect can be detected.

[Fifth Embodiment]

Figure 17:
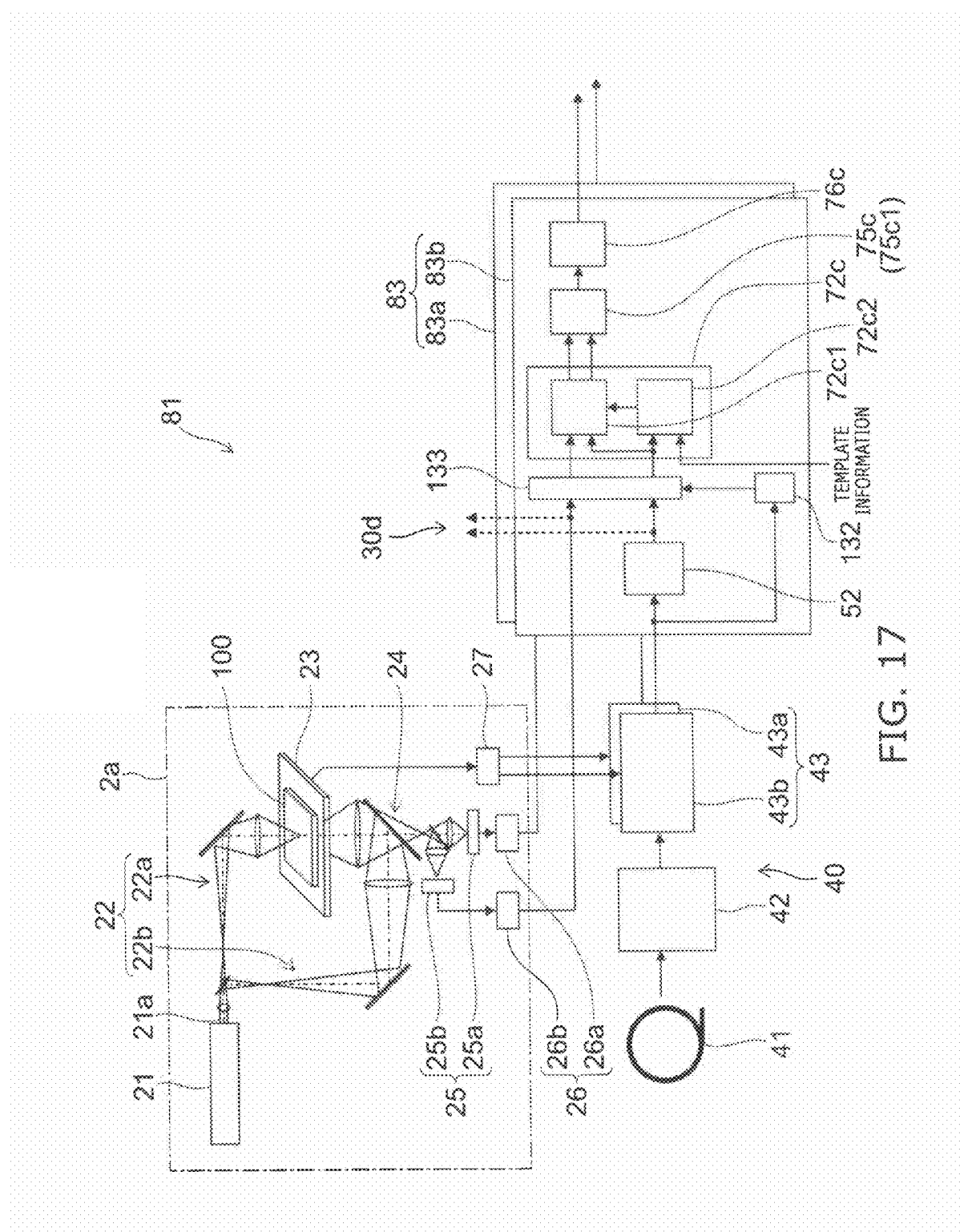
FIG. 17 is a block diagram for illustrating a pattern inspection apparatus according to a fifth embodiment.

FIG. 17 is a block diagram for illustrating a pattern inspection apparatus according to a fifth embodiment. As an example, FIG. 17 illustrates a pattern inspection apparatus for inspecting a pattern using the die-to-database method.

As shown in FIG. 17, the pattern inspection apparatus 81 includes a inspection data creation section 2a, a reference data creation section 40, and an inspection section 83.

The inspection section 83 includes a transmission inspection section 83a for performing inspection using inspection data based on transmitted light, and a reflection inspection section 83b for performing inspection using inspection data based on reflected light.

The elements provided in the transmission inspection section 83a can be made similar to the elements provided in the reflection inspection section 83b. Thus, by way of example, the elements provided in the reflection inspection section 83b are illustrated.

The reflection inspection section 83b includes a gradation conversion section 52, a recognition section 132, an extraction section 133, a pattern extraction section 72c (third pattern extraction section) (pattern extraction section 72c1 and correlation calculation section 72c2), a comparison section 75c, and a determination section 76c (ninth determination section).

Like that described above, the reference data creation section 40 creates reference data. The gradation conversion section 52 converts the output level so that the output level of the reference data corresponds to the output level of the detection section 25. The recognition section 132 recognizes whether or not the inputted reference data is data concerning the image of a sub-resolution pattern. The extraction section 133 outputs the reference data recognized as data of a sub-resolution pattern by the recognition section 132, and the corresponding inspection data toward the pattern extraction section 72c1 and the correlation calculation section 72c2.

The correlation calculation section 72c2 detects a pattern having a specific repetition pitch included in the template information 104 from the inputted sub-resolution pattern by correlation calculation (pattern matching).

The pattern extraction section 72c1 extracts the pattern detected in the correlation calculation section 72c2 from the inspection data and the reference data.

Like that described above, the comparison section 75c includes a level difference calculation section 75c1 (sixth level difference calculation section). The level difference calculation section 75c1 calculates the difference between the inspection data and the reference data inputted from the pattern extraction section 72c1. Then, the level difference calculation section 75c1 outputs the calculated data toward the determination section 76c.

Like that described above, the determination section 76c includes determination sections 76a1, 76a2 and a logic OR calculation section 76a3.

The determination sections 76a1, 76a2 make a determination on the inputted data using two thresholds of an upper bound and a lower bound. For instance, the determination section 76a1 can make a determination using the threshold of the lower bound, and the determination section 76a2 can make a determination using the threshold of the upper bound.

The logic OR calculation section 76a3 calculates the logic OR of the determination result of the determination section 76a1 and the determination result of the determination section 76a2. Thus, if at least one of the determination result of the determination section 76a1 and the determination result of the determination section 76a2 is a determination result representing the presence of a defect, an inspection result representing the presence of a defect is outputted from the logic OR calculation section 76a3.

Although the transmission inspection section 83a and the reflection inspection section 83b are provided in the case illustrated above, it is also possible to provide only one of them. However, more appropriate inspection can be performed by providing the transmission inspection section 83a and the reflection inspection section 83b.

The foregoing refers to the case of inspecting a sub-resolution pattern. In this case, the to-be-inspected pattern may include an optically resolvable pattern. Thus, as shown in FIG. 17, an output section 30d for externally outputting the inspection data and the delay data is provided so that an inspection section, not shown, for inspecting an optically resolvable pattern can be connected to the output section 30d. The inspection section for inspecting an optically resolvable pattern can be based on known techniques, and hence the description thereof is omitted.

According to the embodiment, sufficient inspection sensitivity can be achieved even for an optically unresolvable pattern.

Furthermore, by the correlation calculation section, a pattern having a specific repetition pitch can be detected from the inputted sub-resolution pattern. Based on the detected pattern having a specific repetition pitch, the presence or absence of a defect can be determined.

Here, by comparison between the pattern of the inspection data having a specific repetition pitch and the pattern of the reference data having a specific repetition pitch, comparison inspection can be performed while mutually canceling the variation of the output level of the patterns.

Thus, in a sub-resolution pattern having a specific repetition pitch, a finer defect can be detected.

[Sixth Embodiment]

Next, a structure of a pattern according to a sixth embodiment is illustrated.

First, the influence of e.g. the aforementioned shape condition of the pattern on transmittance and reflectance is illustrated.

Figure 18A:
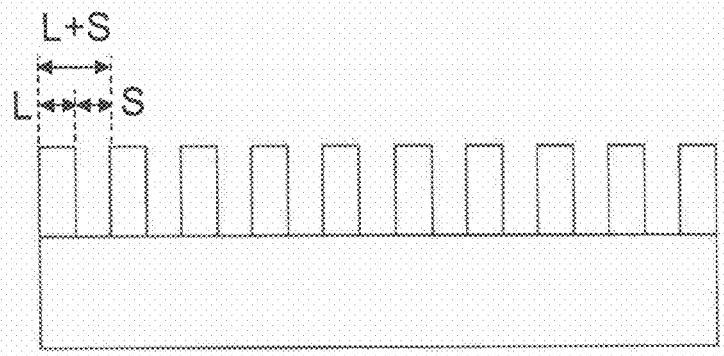
FIG. 18A is a schematic view for illustrating the periodic structure of a pattern targeted.
Figure 18B:
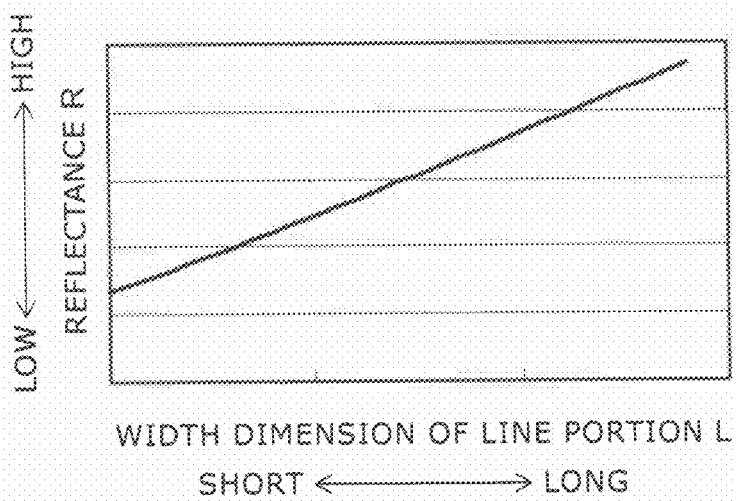
FIG. 18B is a schematic graph for illustrating the relationship between the shape condition of the pattern and reflectance.

FIGS. 18A and 18B are schematic views for illustrating the relationship between the shape condition of the pattern and reflectance.

More specifically, FIG. 18A is a schematic view for illustrating the periodic structure of a sub-resolution fine pattern targeted in the embodiment. FIG. 18B is a schematic graph for illustrating the relationship between the shape condition of the pattern and reflectance.

As shown in FIG. 18A, in the case of a sub-resolution line-and-space pattern, it is known that the refractive index depends on the polarization of light. For instance, in the case of a TE wave where the oscillation direction of the electric field is parallel to the pattern, the refractive index n' is given by the following equation (1):

$$n' = \sqrt{\frac{L \cdot n1^2 + S \cdot n2^2}{L+S}} \quad (1)$$

where L is the width dimension of the line portion, S is the width dimension of the space portion, L+S is the pitch dimension of the pattern, n1 is the refractive index of the line portion, and n2 is the refractive index of the space portion.

In the case of e.g. glass where the extinction coefficient (k) is zero, the reflectance R is given by the following equation (2):

$$R = \frac{(1-n')^2}{(1+n')^2} \quad (2)$$

Here, it is assumed that the material of the line portion is glass, the space portion is air, and the pitch dimension of the pattern (L+S) is constant (e.g., 48 nm). Then, the reflectance determined from equations (1) and (2) as a function of the width dimension L of the line portion is as shown in FIG. 18B.

As seen from FIG. 18B, even if the pitch dimension of the pattern is equal, the reflectance varies with the width dimension L of the line portion. That is, the reflectance varies with the ratio of the line portion to the space portion. This means that the ratio of the line portion to the space portion, and the width dimension of the line portion due to e.g. process conditions, for instance, can be inspected by measuring the reflectance.

Figure 19A:
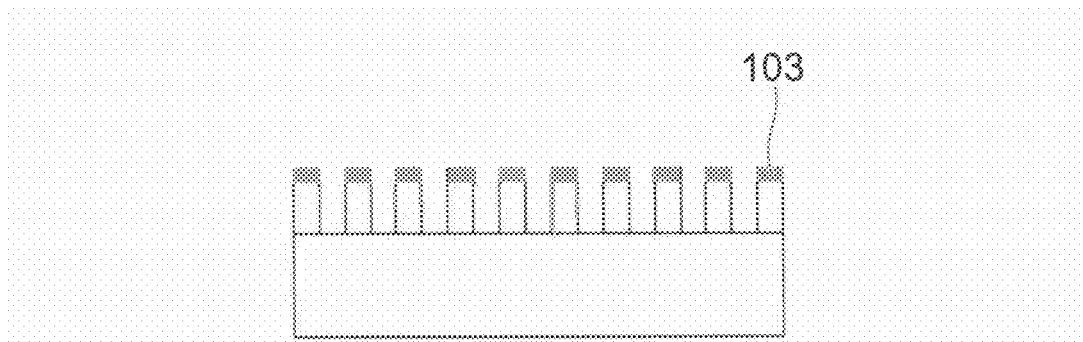
FIGS. 19A and 19B are schematic views for illustrating the relationship between the proportion occupied by a thin layer on the surface and reflectance/transmittance.
Figure 19B:
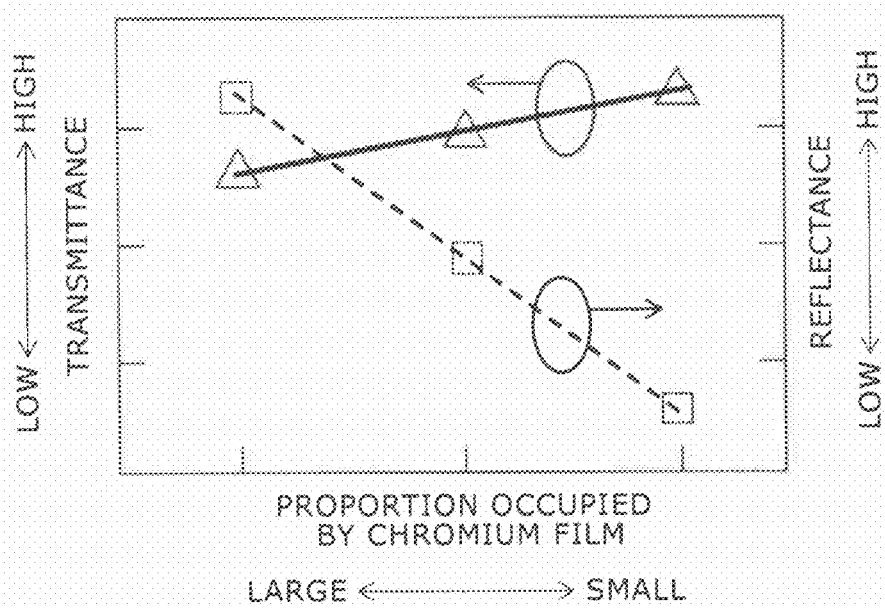

FIGS. 19A and 19B are schematic views for illustrating the relationship between the proportion occupied by a thin layer on the surface and reflectance/transmittance.

More specifically, FIG. 19A is a schematic view for illustrating the structure of a pattern with a thin layer on the surface. FIG. 19B is a schematic graph for illustrating the relationship between the proportion occupied by the thin layer on the surface of the pattern and reflectance/transmittance.

As shown in FIG. 19A, it is assumed that a line-and-space pattern is formed on the surface of a glass substrate. A chromium (Cr) layer 103, for instance, is provided on the surface of the pattern (above the line-and-space).

In such a case, the reflectance of the chromium layer 103 is several times higher than the reflectance of glass. Hence, the presence of the chromium layer 103 exerts a greater influence on reflectance and transmittance than the aforementioned dimensional variation of the line portion (the portion made of glass).

For instance, as shown in FIG. 19B, increasing the proportion occupied by the chromium layer 103 results in lower transmittance and higher reflectance. Decreasing the proportion occupied by the chromium layer 103 results in higher transmittance and lower reflectance.

This also applies to the case where the thin layer on the surface is made of a material other than chromium (Cr). However, the value depends on the optical constants (n, k) of the material of the thin layer on the surface.

Thus, transmittance and reflectance vary with the proportion occupied by the thin layer on the surface. This means that the proportion occupied by the thin layer on the surface can be inspected by measuring the transmittance and reflectance.

Figure 20A:
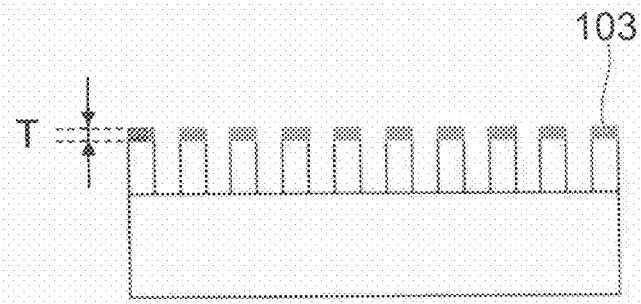
FIG. 20A is a schematic view for illustrating the structure of a pattern with a thin layer on the surface.
Figure 20B:
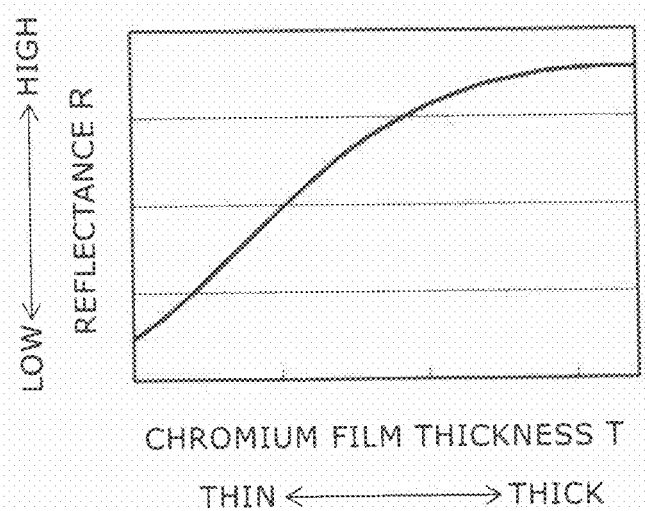
FIG. 20B is a schematic graph for illustrating the relationship between the thickness of the thin layer on the surface of the pattern and reflectance.

FIGS. 20A and 20B are schematic views for illustrating the relationship between the thickness of a thin layer on the surface and reflectance. More specifically, FIG. 20A is a schematic view for illustrating the structure of a pattern with a thin layer on the surface. FIG. 20B is a schematic graph for illustrating the relationship between the thickness of the thin layer on the surface of the pattern and reflectance.

As shown in FIG. 20A, a line-and-space pattern is formed on the surface of a glass substrate. A chromium (Cr) layer 103, for instance, is provided on the surface of the pattern (above the line-and-space). The thickness of the chromium layer 103 is denoted by T.

FIG. 20B illustrates the result obtained by optical simulation of the relationship between the thickness of the chromium layer 103 on the surface of the pattern and reflectance.

As shown in FIG. 20B, the reflectance varies with the thickness T of the chromium layer 103. Hence, the reflectance can be controlled by controlling the thickness T of the chromium layer 103. This means that the thickness T of the chromium layer 103 can be inspected by measuring the reflectance.

Figure 21A:
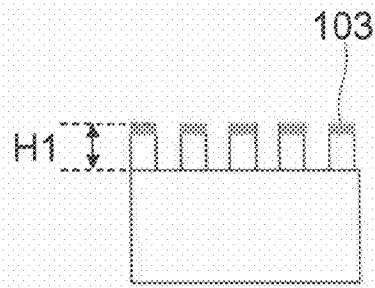
FIGS. 21A and 21B are schematic views for illustrating the structure of a pattern with a thin layer on the surface.
Figure 21B:
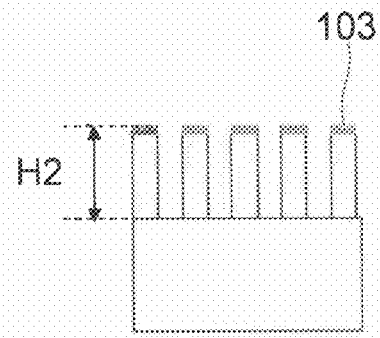
Figure 21C:
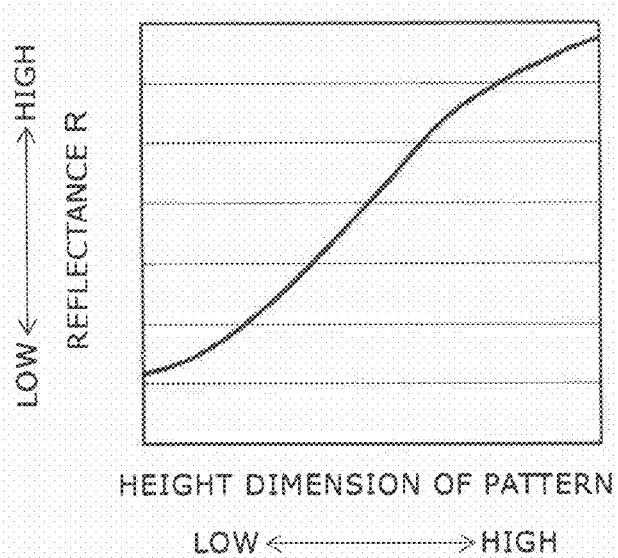
FIG. 21C is a schematic graph for illustrating the relationship between the height dimension of the pattern and reflectance.

FIGS. 21A to 21C are schematic views for illustrating the relationship between the height dimension of a pattern and reflectance.

More specifically, FIGS. 21A and 21B are schematic views for illustrating the structure of a pattern with a thin layer on the surface. FIG. 21C is a schematic graph for illustrating the relationship between the height dimension of the pattern and reflectance. The thin layer on the surface of the pattern is a chromium layer 103.

The reflectance is different between in the case where the height dimension H1 of the pattern is low as shown in FIG. 21A, and in the case where the height dimension H2 of the pattern is high as shown in FIG. 21B.

For instance, in the case where the height dimension of the pattern is ¼ of the wavelength of the inspection light 21a, the reflectance is made lower by destructive interference of reflected light beams. In the case where the height dimension of the pattern is ½ of the wavelength of the inspection light 21a, the reflectance is made higher by constructive interference of reflected light beams. Thus, optical simulation is performed for the height dimension of the pattern between ¼ and ½ of the wavelength of the inspection light 21a to determine the relationship between the height dimension of the pattern and reflectance. FIG. 21C illustrates the result of the optical simulation.

As shown in FIG. 21C, the reflectance varies with the height dimension of the pattern. Hence, the reflectance can be controlled by controlling the height dimension of the pattern. This means that the height dimension of the pattern can be inspected by measuring the reflectance.

As illustrated above, the shape condition of the pattern such as the ratio of the line portion to the space portion and the height dimension of the pattern, the proportion occupied by the thin layer on the surface, and the thickness of the layer, for instance, can be inspected by measuring the reflectance and transmittance.

Thus, in the pattern inspection apparatus illustrated in FIGS. 11 and 12, the degree of change of transmittance and reflectance is measured by the average level difference calculation section and the distribution collect section. Based thereon, the determination section 65 inspects e.g. the change of e.g. the shape condition of the pattern such as the ratio of the line portion to the space portion and the height dimension of the pattern, the proportion occupied by the thin layer on the surface, and the thickness of the layer (such as the change of the pattern line width and the change of the process condition during pattern formation).

Here, the S/N ratio of inspection data obtained by the pattern inspection apparatus is determined by the ratio of the signal level of the inspection data to the noise level. Thus, in the S/N ratio of the inspection data (inspection image), if the signal level of the inspection data is low, the noise level is dominant. More specifically, the S/N ratio is high if the signal level of the inspection data is high, and the S/N ratio is low if the signal level of the inspection data is low.

That is, in the case where a sub-resolution pattern is inspected by the pattern inspection apparatus, the signal level of the inspection data can be increased by increasing the reflectance and transmittance. Hence, the S/N ratio of the inspection data (inspection image) can be increased.

Thus, in the structure of a pattern according to the embodiment, the shape condition of the pattern such as the ratio of the line portion to the space portion and the height dimension of the pattern, the proportion occupied by the thin layer on the surface, and the thickness of the layer, for instance, are controlled so as to increase at least one of the reflectance and transmittance.

In the structure of a pattern according to the embodiment, the reflectance and transmittance can be increased. Hence, pattern inspection with high S/N ratio can be performed in the pattern inspection apparatus described above or the pattern inspection method described below.

Thus, sufficient inspection sensitivity can be achieved even for an optically unresolvable pattern. Furthermore, a finer defect can be inspected.

Next, pattern inspection methods according to the present embodiments are illustrated.

Here, creation of data, recognition of a sub-resolution pattern, and determination of the presence or absence of a defect, for instance, performed in the steps of the embodiments illustrated below are similar to those illustrated in the aforementioned pattern inspection apparatuses, and hence the detailed description thereof is omitted.

[Seventh Embodiment]

Next, a pattern inspection method according to a seventh embodiment is illustrated.

The pattern inspection method according to the embodiment can be performed in e.g. the inspection section 3 illustrated in FIG. 1.

Figure 22:
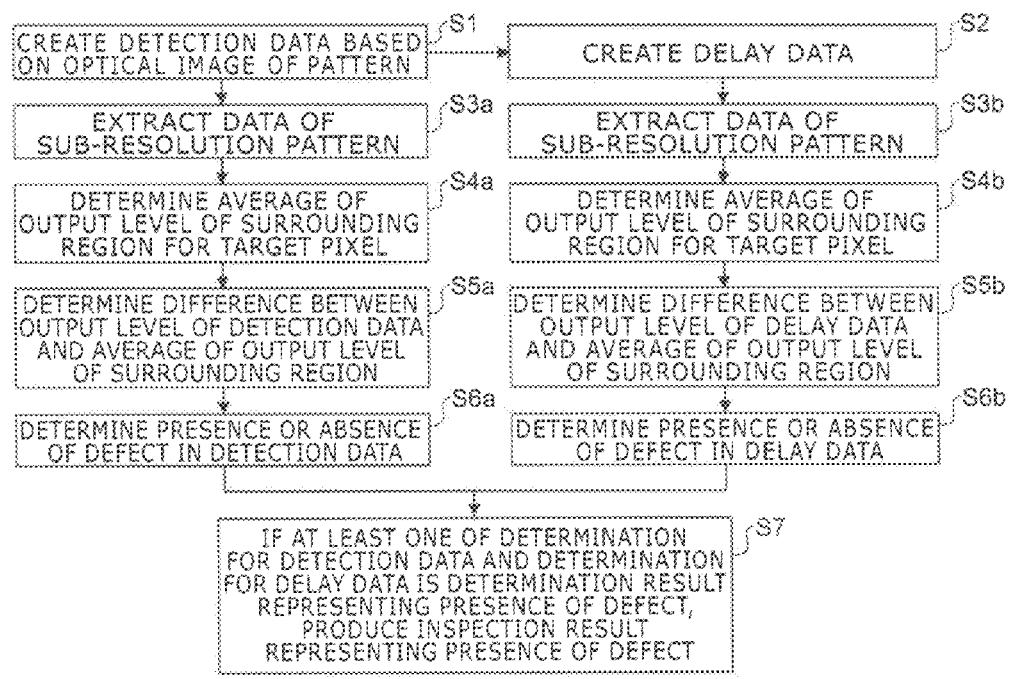
FIG. 22 is a flow chart for illustrating a pattern inspection method according to a seventh embodiment.

FIG. 22 is a flow chart for illustrating the pattern inspection method according to the seventh embodiment.

First, inspection data is created based on the optical image of a pattern formed on a to-be-inspected object 100 (step S1).

Next, the inspection data is delayed to create delay data (step S2).

More specifically, delay data is created by inserting a certain time delay in the transfer of the inspection data without changing the waveform of the electrical signal of the inspection data.

Next, data of a sub-resolution pattern is extracted from the inspection data (step S3a). Recognition of whether or not the given data is data of a sub-resolution pattern can be performed based on the output level of the inspection data.

For a target pixel of the extracted inspection data, the average of the output level of the surrounding region for a target pixel is calculated (step S4a).

The difference between the output level of a target pixel of the extracted inspection data and the average of the output level of the surrounding region for a target pixel is calculated (step S5a).

Based on the calculated value, the presence or absence of a defect in the inspection data is determined (step S6a).

That is, the presence or absence of a defect in the inspection data is determined based on the difference between the output level of a target pixel of the extracted inspection data and the average of the output level of the surrounding region for a target pixel.

For instance, the presence or absence of a defect can be determined using two thresholds of an upper bound and a lower bound.

On the other hand, data of a sub-resolution pattern is extracted from the delay data (step S3b). Recognition of whether or not the given data is data of a sub-resolution pattern can be performed based on the output level of the delay data.

For a target pixel of the extracted delay data, the average of the output level of the surrounding region for a target pixel of the extracted delay data is calculated (step S4b).

The difference between the output level of a target pixel of the extracted delay data and the average of the output level of the surrounding region for a target pixel of the extracted delay data is calculated (step S5b).

Based on the calculated value, the presence or absence of a defect in the delay data is determined (step S6b).

That is, the presence or absence of a defect in the delay data is determined based on the difference between the output level of a target pixel of the extracted delay data and the average of the output level of the surrounding region for a target pixel of the extracted delay data.

For instance, the presence or absence of a defect can be determined using two thresholds of an upper bound and a lower bound.

Next, if at least one of the determination for the inspection data and the determination for the delay data is a determination result representing the presence of a defect, an inspection result representing the presence of a defect is produced (step S7).

That is, a defect inspection result is determined based on the determination result of the step of determining the presence or absence of a defect in the inspection data and the determination result of the step of determining the presence or absence of a defect in the delay data.

Here, the inspection data may be created based on an optical image formed by transmitted light or an optical image formed by reflected light.

According to the embodiment, sufficient inspection sensitivity can be achieved even for an optically unresolvable pattern.

Furthermore, the output level of the surrounding region can be flattened by calculating the difference between the output level of the inspection data and the average of the output level of the surrounding region, and the difference between the output level of the delay data and the average of the output level of the surrounding region. Thus, the S/N ratio in defect determination can be increased. Hence, a finer defect can be determined.

[Eighth Embodiment]

Next, a pattern inspection method according to an eighth embodiment is illustrated.

The pattern inspection method according to the embodiment can be performed in e.g. the inspection section 13 illustrated in FIG. 6.

Figure 23:
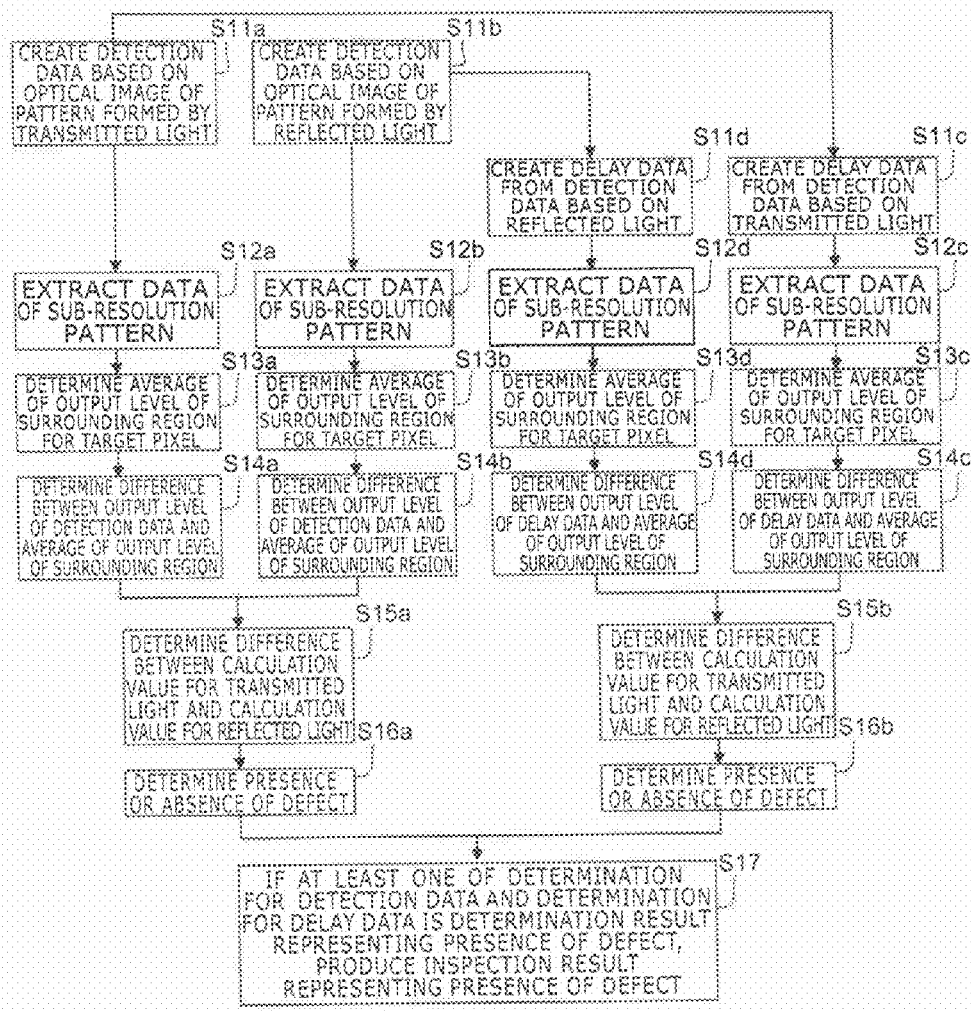
FIG. 23 is a flow chart for illustrating a pattern inspection method according to an eighth embodiment.

FIG. 23 is a flow chart for illustrating the pattern inspection method according to the eighth embodiment.

The pattern inspection method according to the embodiment uses both of inspection data created based on an optical image formed by transmitted light and inspection data created based on an optical image formed by reflected light.

First, inspection data is created based on the optical image of a pattern formed by transmitted light (step S11a).

Next, data of a sub-resolution pattern is extracted from the inspection data (first extraction step) (step S12a).

For a target pixel of the extracted data, the average of the output level of the surrounding region is calculated (first calculation step) (step S13a).

The difference between the output level of a target pixel of the data extracted in step S12a and the average of the output level of the surrounding region for a pixel of the extracted data calculated in step S13a is calculated (second calculation step) (step S14a).

On the other hand, inspection data is created based on the optical image of the pattern formed by reflected light (step S11b).

Next, data of a sub-resolution pattern is extracted from the inspection data (second extraction step) (step S12b).

For a target pixel of the extracted data, the average of the output level of the surrounding region is calculated (third calculation step) (step S13b).

The difference between the output level of a target pixel of the data extracted in step S12b and the average of the output level of the surrounding region for a target pixel of the extracted data calculated in step S13b is calculated (fourth calculation step) (step S14b).

On the other hand, the inspection data based on transmitted light is delayed to create delay data (step S11c).

Next, data of a sub-resolution pattern is extracted from the delay data (third extraction step) (step S12c).

For a target pixel of the extracted data, the average of the output level of the surrounding region is calculated (fifth calculation step) (step S13c).

The difference between the output level of a target pixel of the data extracted in step S12c and the average of the output level of the surrounding region for a target pixel of the extracted data calculated in step S13c is calculated (sixth calculation step) (step S14c).

On the other hand, the inspection data based on reflected light is delayed to create delay data (step S11d).

Next, data of a sub-resolution pattern is extracted from the delay data (fourth extraction step) (step S12d).

For a target pixel of the extracted data, the average of the output level of the surrounding region is calculated (seventh calculation step) (step S13d).

The difference between the output level of a target pixel of the data extracted in step S12d and the average of the output level of the surrounding region for a target pixel of the extracted data calculated in step S13d is calculated (eighth calculation step) (step S14d).

Next, the difference between the calculation value of step S14a and the calculation value of step S14b is calculated (ninth calculation step) (step S15a).

That is, with regard to the inspection data, the difference between the calculation value for transmitted light and the calculation value for reflected light is calculated.

Based on the calculation value of step S15a, the presence or absence of a defect for the inspection data is determined (first determination step) (step S16a).

On the other hand, the difference between the calculation value of step S14c and the calculation value of step S14d is calculated (tenth calculation step) (step S15b).

That is, with regard to the delay data, the difference between the calculation value for transmitted light and the calculation value for reflected light is calculated.

Based on the calculation value of step S15b, the presence or absence of a defect for the delay data is determined (second determination step) (step S16b).

For instance, the presence or absence of a defect can be determined using two thresholds of an upper bound and a lower bound.

Next, a defect inspection result is determined based on the determination result of step S16a and the determination result of step S16b (step S17).

Here, if at least one of the determination for the inspection data and the determination for the delay data is a determination result representing the presence of a defect, an inspection result representing the presence of a defect can be produced.

According to the embodiment, sufficient inspection sensitivity can be achieved even for an optically unresolvable pattern.

Furthermore, the output level of the surrounding region can be flattened by calculating the difference between the output level of the inspection data and the average of the output level of the surrounding region, and the difference between the output level of the delay data and the average of the output level of the surrounding region. Thus, the S/N ratio in defect determination can be increased. Hence, a finer defect can be determined.

Furthermore, the defect portion can be enhanced by calculating the difference between the data based on transmitted light and the data based on reflected light (summing them with the polarity of one of them inverted). Thus, the S/N ratio in defect determination can be further increased. Hence, an even finer defect can be determined.

[Ninth Embodiment]

Next, a pattern inspection method according to a ninth embodiment is illustrated.

The pattern inspection method according to the embodiment can be performed in e.g. the inspection section 53 illustrated in FIG. 8.

Figure 24:
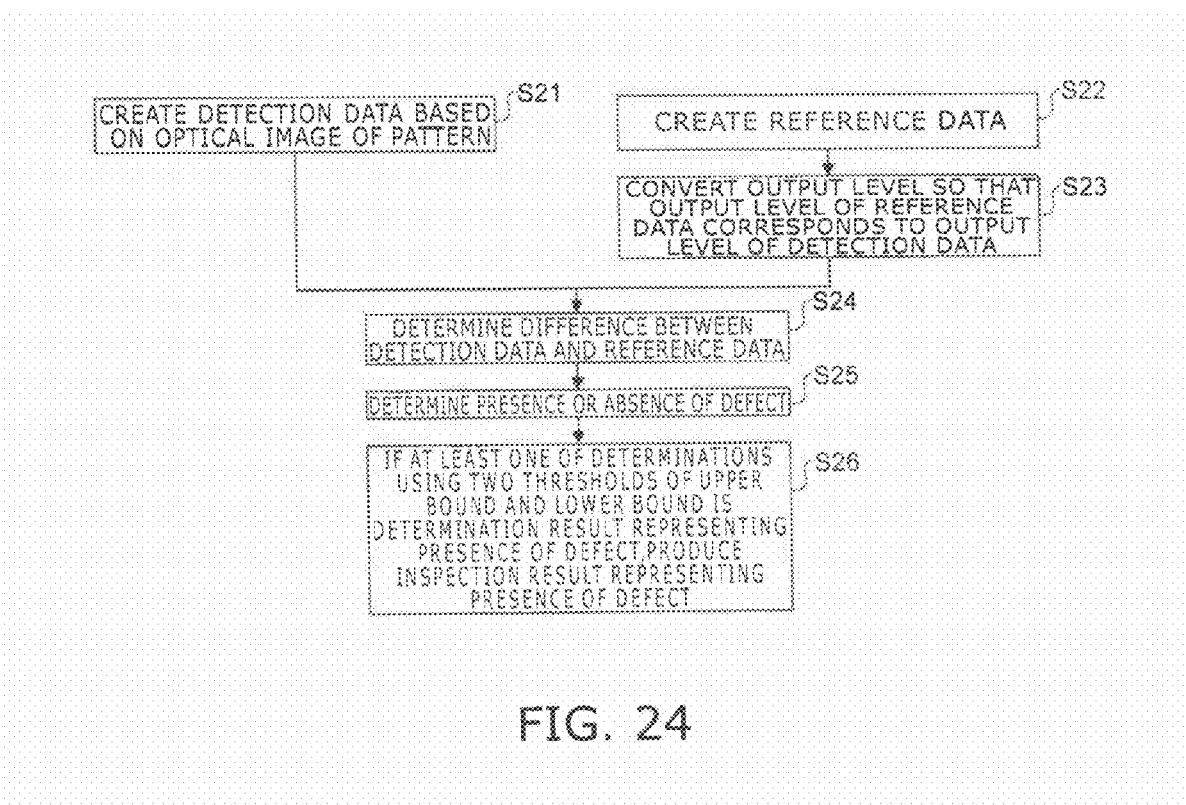
FIG. 24 is a flow chart for illustrating a pattern inspection method according to a ninth embodiment.

FIG. 24 is a flow chart for illustrating the pattern inspection method according to the ninth embodiment.

First, inspection data is created based on the optical image of a pattern formed on a to-be-inspected object 100 (step S21).

On the other hand, reference data concerning the pattern formed on the to-be-inspected object 100 is created (step S22).

Next, the output level is converted so that the output level of the reference data corresponds to the output level of the inspection data (step S23).

Here, the output level can be converted using a predetermined gradation conversion table. The gradation conversion table can be previously determined by e.g. experiment or simulation.

Next, the difference between the inspection data and the reference data whose output level has been converted is determined (step S24).

Based on the determined value, the presence or absence of a defect is determined (step S25).

For instance, the presence or absence of a defect can be determined using two thresholds of an upper bound and a lower bound.

Next, if at least one of the determinations using two thresholds of the upper bound and the lower bound is a determination result representing the presence of a defect, an inspection result representing the presence of a defect is produced (step S26).

Here, the inspection data may be created based on an optical image formed by transmitted light or an optical image formed by reflected light.

According to the embodiment, sufficient inspection sensitivity can be achieved even for an optically unresolvable pattern.

Furthermore, the output level is converted so that the output level of the reference data corresponds to the output level of the inspection data. Thus, the inspection accuracy can be improved. Hence, a finer defect can be determined.

[Tenth Embodiment]

Next, a pattern inspection method according to a tenth embodiment is illustrated.

The pattern inspection method according to the embodiment can be performed in e.g. the inspection section 153 illustrated in FIG. 10.

Figure 25:
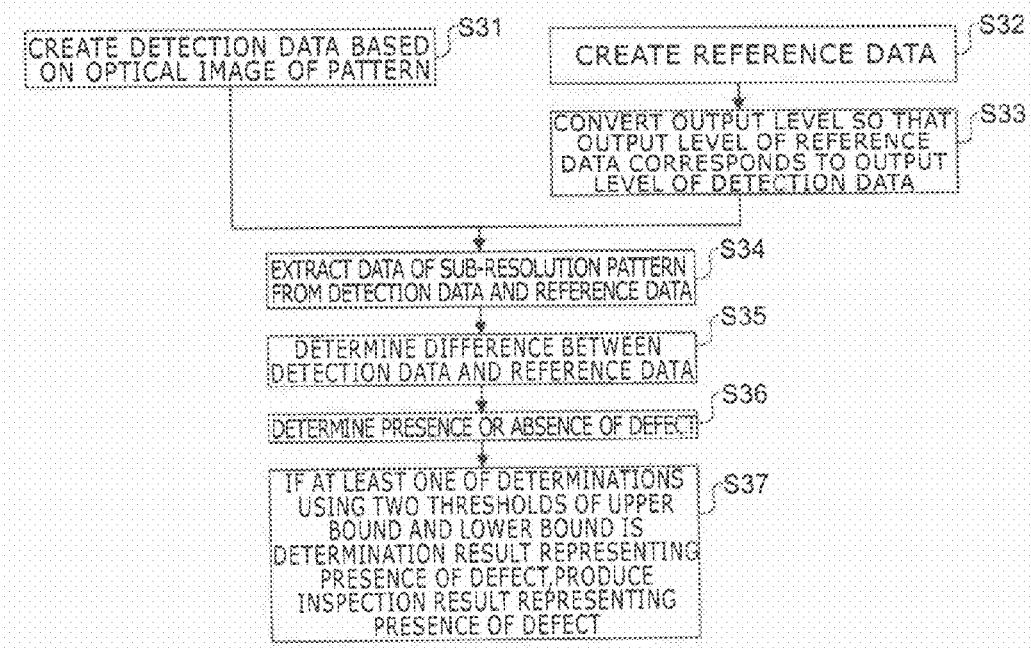
FIG. 25 is a flow chart for illustrating a pattern inspection method according to a tenth embodiment.

FIG. 25 is a flow chart for illustrating the pattern inspection method according to the tenth embodiment.

First, inspection data is created based on the optical image of a pattern formed on a to-be-inspected object 100 (step S31).

On the other hand, reference data concerning the pattern formed on the to-be-inspected object 100 is created (step S32).

Next, the output level is converted so that the output level of the reference data corresponds to the output level of the inspection data (step S33).

Here, the output level can be converted using a predetermined gradation conversion table. The gradation conversion table can be previously determined by e.g. experiment or simulation.

Next, data of a sub-resolution pattern is extracted from the inspection data and the reference data (step S34).

The extraction of data of a sub-resolution pattern can be performed in the following procedure. First, it is recognized whether or not the reference data is data concerning the image of a sub-resolution pattern (first recognition step).

Next, based on the recognition result of the first recognition step, data of a sub-resolution pattern is extracted from the inspection data and the reference data (fifth extraction step).

The recognition of whether or not the given data is data of a sub-resolution pattern can be performed based on the output level of the reference data. Here, a similar recognition result can be applied to the inspection data corresponding to the reference data.

Next, the difference between the extracted inspection data and the extracted reference data is calculated (step S35).

Based on the calculated value, the presence or absence of a defect is determined (step S36).

For instance, the presence or absence of a defect can be determined using two thresholds of an upper bound and a lower bound.

Next, if at least one of the determinations using two thresholds of the upper bound and the lower bound is a determination result representing the presence of a defect, an inspection result representing the presence of a defect is produced (step S37).

Here, the inspection data may be created based on an optical image formed by transmitted light or an optical image formed by reflected light.

According to the embodiment, sufficient inspection sensitivity can be achieved even for an optically unresolvable pattern.

Furthermore, the output level is converted so that the output level of the reference data corresponds to the output level of the inspection data. Thus, the inspection accuracy can be improved. Hence, a finer defect can be determined.

Furthermore, data of a sub-resolution pattern is extracted from the inspection data and the reference data. Hence, an optically unresolvable pattern, which is conventionally difficult to inspect, can be preferentially inspected.

[Eleventh Embodiment]

Next, a pattern inspection method according to an eleventh embodiment is illustrated.

The pattern inspection method according to the embodiment can be performed in e.g. the inspection section 63 illustrated in FIG. 11.

Figure 26:
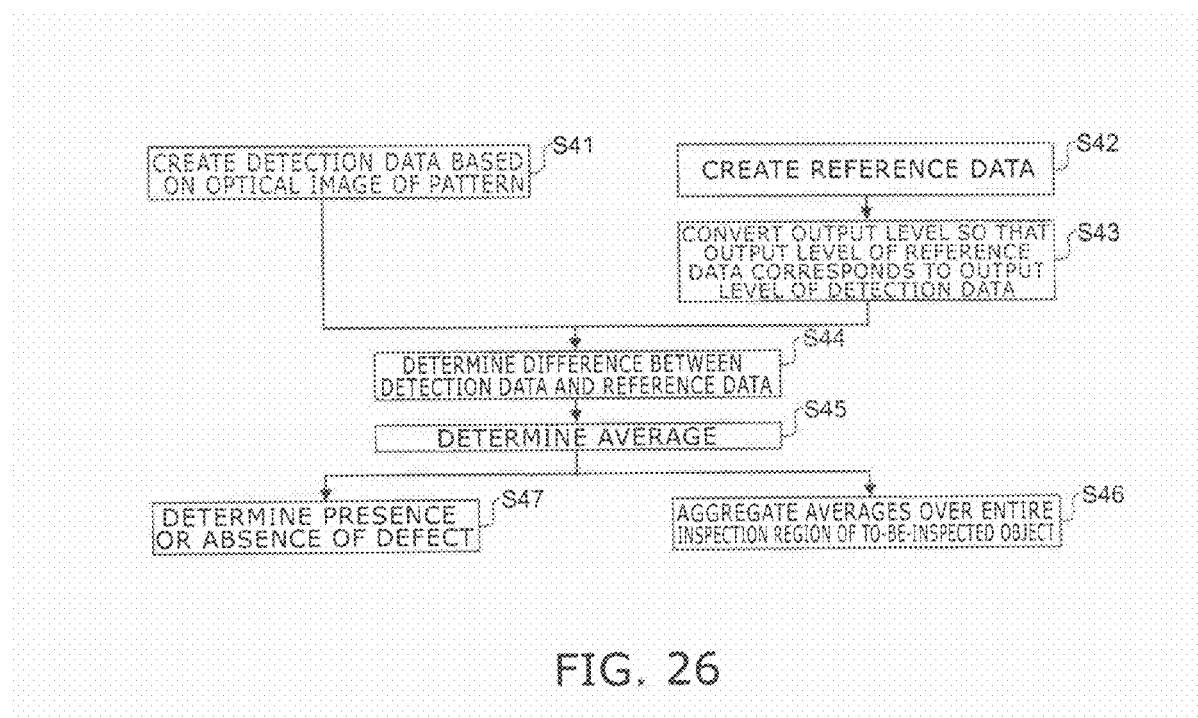
FIG. 26 is a flow chart for illustrating a pattern inspection method according to an eleventh embodiment.

FIG. 26 is a flow chart for illustrating the pattern inspection method according to the eleventh embodiment.

First, inspection data is created based on the optical image of a pattern formed on a to-be-inspected object 100 (step S41).

On the other hand, reference data concerning the pattern formed on the to-be-inspected object 100 is created (step S42).

Next, the output level is converted so that the output level of the reference data corresponds to the output level of the inspection data (step S43).

Here, the output level can be converted using a predetermined gradation conversion table. The gradation conversion table can be previously determined by e.g. experiment or simulation.

Next, the difference between the inspection data and the reference data whose output level has been converted is calculated (eleventh calculation step) (step S44).

Next, the average of the calculation value of step S44 is calculated (twelfth calculation step) (step S45).

Here, the average in a certain predetermined region (e.g., a region of N pixels×N pixels in the inspection data) is calculated.

Next, the calculated averages are collected over the entire inspection region of the to-be-inspected object 100 (step S46).

Here, the collected information can also be displayed on e.g. the display section 66.

By thus aggregating data over the entire inspection region of the to-be-inspected object 100, the degree of change of transmittance and reflectance of the sub-resolution pattern can be measured.

Then, by measuring the degree of change of transmittance and reflectance of the sub-resolution pattern, the change of the pattern line width and the change of the process condition during pattern formation can be inspected. Furthermore, abnormality factors in the manufacturing process, for instance, can also be found.

Furthermore, for instance, the change of the process condition in the writing process and etching process during pattern formation can be measured. Thus, the condition for reducing the change can be fed back to the writing process and etching process during pattern formation.

In the case where such a patterned object is used to manufacture another product, the changed pattern line width, for instance, can be fed forward to the downstream process to increase the yield of the product. For instance, in the case where the to-be-inspected object 100 is a photomask, the changed pattern line width, for instance, can be fed forward to the lithography process to increase the yield of e.g. semiconductor devices.

On the other hand, based on the calculated average, the presence or absence of a defect is determined (step S47).

For instance, the presence or absence of a defect can be determined using two thresholds of an upper bound and a lower bound.

In this case, if at least one of the determinations using two thresholds of the upper bound and the lower bound is a determination result representing the presence of a defect, an inspection result representing the presence of a defect can be produced.

Here, the inspection data may be created based on an optical image formed by transmitted light or an optical image formed by reflected light.

According to the embodiment, sufficient inspection sensitivity can be achieved even for an optically unresolvable pattern.

Furthermore, the degree of change of transmittance and reflectance of a sub-resolution pattern can be measured. Thus, it is possible to inspect the shape condition of the pattern such as the ratio of the line portion to the space portion and the height dimension of the pattern, the proportion occupied by the thin layer provided on the surface, and the thickness of the thin layer (such as the change of the pattern line width and the change of the process condition during pattern formation). Furthermore, abnormality factors in the manufacturing process, for instance, can also be found. Furthermore, the condition for reducing the change can be fed back to the process for forming the pattern. Furthermore, the changed pattern line width, for instance, can be fed forward to the downstream process. Thus, the yield of products can be increased.

Furthermore, the output level is converted so that the output level of the reference data corresponds to the output level of the inspection data. Thus, the inspection accuracy can be improved. Hence, a finer defect can be determined.

[Twelfth Embodiment]

Next, a pattern inspection method according to a twelfth embodiment is illustrated.

The pattern inspection method according to the embodiment can be performed in e.g. the inspection section 163 illustrated in FIG. 12.

Figure 27:
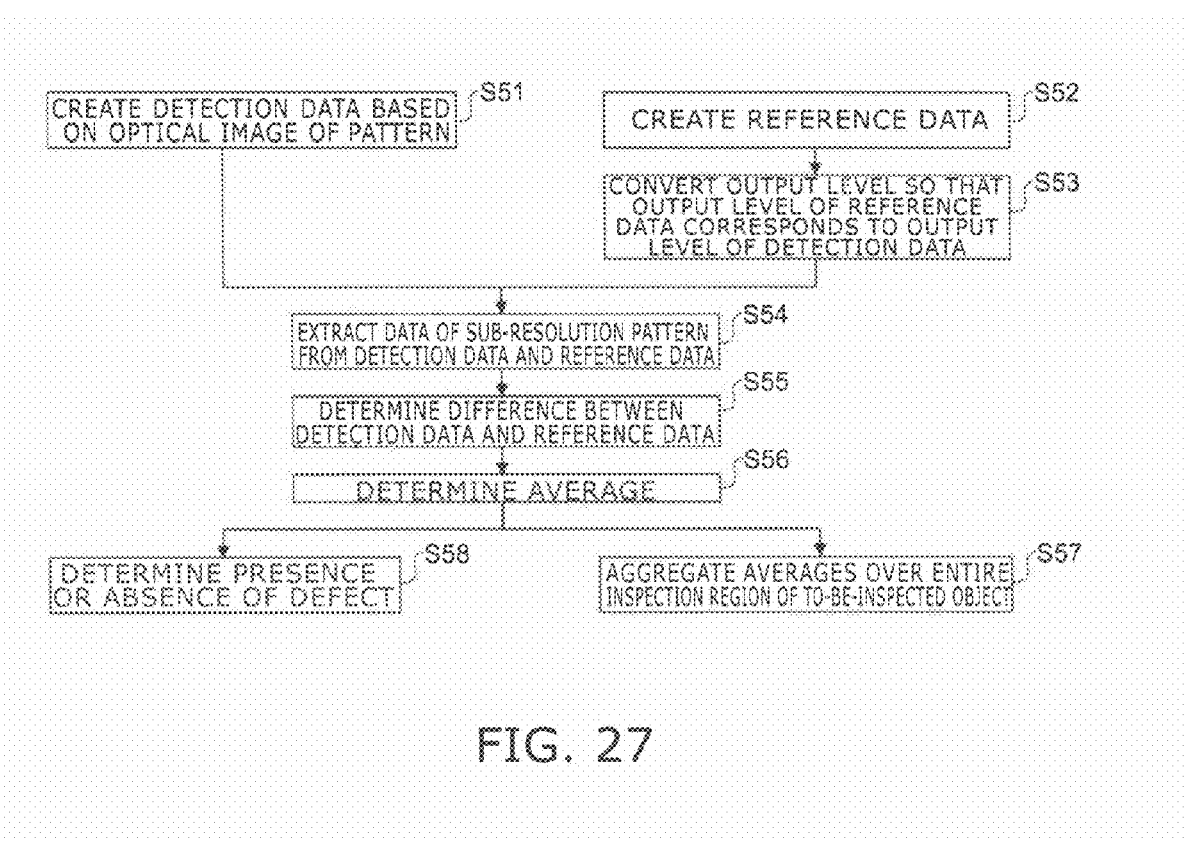
FIG. 27 is a flow chart for illustrating a pattern inspection method according to a twelfth embodiment.

FIG. 27 is a flow chart for illustrating the pattern inspection method according to the twelfth embodiment.

First, inspection data is created based on the optical image of a pattern formed on a to-be-inspected object 100 (step S51).

On the other hand, reference data concerning the pattern formed on the to-be-inspected object 100 is created (step S52).

Next, the output level is converted so that the output level of the reference data corresponds to the output level of the inspection data (step S53).

Here, the output level can be converted using a predetermined gradation conversion table. The gradation conversion table can be previously determined by e.g. experiment or simulation.

Next, data of a sub-resolution pattern is extracted from the inspection data and the reference data (step S54).

The extraction of data of a sub-resolution pattern can be performed in the following procedure. First, it is recognized whether or not the inspection data and the reference data are data concerning the image of a sub-resolution pattern (second recognition step).

Next, based on the recognition result of the second recognition step, data of a sub-resolution pattern is extracted from the inspection data and the reference data (sixth extraction step).

The recognition of whether or not the given data is data of a sub-resolution pattern can be performed based on the output level of the reference data. Here, a similar recognition result can be applied to the inspection data corresponding to the reference data.

Next, the difference between the extracted inspection data and the extracted reference data is calculated (step S55).

Next, the average of the calculated values is calculated (step S56).

Here, the average in a certain predetermined region (e.g., a region of N pixels×N pixels in the inspection data) is calculated.

Next, the calculated averages are collected over the entire inspection region of the to-be-inspected object 100 (step S57).

Here, the collected information can also be displayed on e.g. the display section 66.

On the other hand, based on the calculated average, the presence or absence of a defect is determined (step S58).

For instance, the presence or absence of a defect can be determined using two thresholds of an upper bound and a lower bound.

In this case, if at least one of the determinations using two thresholds of the upper bound and the lower bound is a determination result representing the presence of a defect, an inspection result representing the presence of a defect can be produced.

Here, the inspection data may be created based on an optical image formed by transmitted light or an optical image formed by reflected light.

According to the embodiment, sufficient inspection sensitivity can be achieved even for an optically unresolvable pattern.

Furthermore, the degree of change of transmittance and reflectance of a sub-resolution pattern can be measured. Thus, it is possible to inspect the shape condition of the pattern such as the ratio of the line portion to the space portion and the height dimension of the pattern, the proportion occupied by the thin layer provided on the surface, and the thickness of the thin layer (such as the change of the pattern line width and the change of the process condition during pattern formation). Furthermore, abnormality factors in the manufacturing process, for instance, can also be found. Furthermore, the condition for reducing the change can be fed back to the process for forming the pattern. Furthermore, the changed pattern line width, for instance, can be fed forward to the downstream process. Thus, the yield of products can be increased.

Furthermore, the output level is converted so that the output level of the reference data corresponds to the output level of the inspection data. Thus, the inspection accuracy can be improved. Hence, a finer defect can be determined.

Furthermore, data of a sub-resolution pattern is extracted from the inspection data and the reference data. Hence, an optically unresolvable pattern, which is conventionally difficult to inspect, can be preferentially inspected.

[Thirteenth Embodiment]

Next, a pattern inspection method according to a thirteenth embodiment is illustrated.

The pattern inspection method according to the embodiment can be performed in e.g. the inspection section 73 illustrated in FIG. 14.

Figure 28:
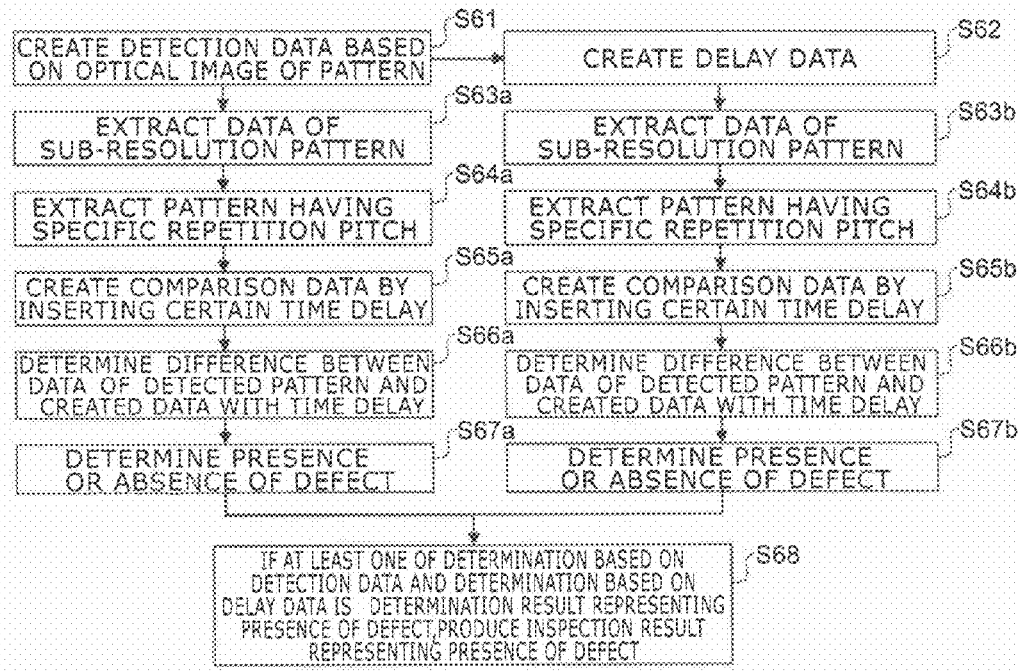
FIG. 28 is a flow chart for illustrating a pattern inspection method according to a thirteenth embodiment.

FIG. 28 is a flow chart for illustrating the pattern inspection method according to the thirteenth embodiment.

First, inspection data is created based on the optical image of a pattern formed on a to-be-inspected object 100 (step S61).

Next, the inspection data is delayed to create delay data (step S62). More specifically, delay data is created by inserting a certain time delay in the transfer of the inspection data without changing the waveform of the electrical signal of the inspection data.

Next, a sub-resolution pattern is extracted from the inspection data (seventh extraction step) (step S63*a*).

Recognition of whether or not the given data is data of a sub-resolution pattern can be performed based on the output level of the inspection data.

Next, a pattern having a specific repetition pitch is extracted from the extracted sub-resolution pattern (eighth extraction step) (step S64*a*).

Here, the extraction of the pattern can be performed by correlation calculation (pattern matching) using a fixed template or the aforementioned variable template.

Next, the data of the pattern having a specific repetition pitch extracted in step S64*a* is delayed to create comparison data (first comparison data) (first delay step) (step S65*a*).

More specifically, a certain time delay is inserted in the transfer of the data of the detected pattern to create data for comparison with data of a subsequently detected pattern.

Next, the difference between the pattern having a specific repetition pitch extracted in step S64*a* and the first comparison data is calculated (thirteenth calculation step) (step S66*a*).

Next, based on the calculation result of step S66*a*, the presence or absence of a defect is determined (third determination step) (step S67*a*).

Here, the determination can be made using two thresholds of an upper bound and a lower bound.

On the other hand, data of a sub-resolution pattern is extracted from the delay data (ninth extraction step) (step S63*b*).

Recognition of whether or not the given data is data of a sub-resolution pattern can be performed based on the output level of the delay data.

Next, a pattern having a specific repetition pitch is extracted from the extracted sub-resolution pattern (tenth extraction step) (step S64*b*).

Here, the extraction of the pattern can be performed by correlation calculation (pattern matching) using a fixed template or the aforementioned variable template.

Next, the data of the pattern having a specific repetition pitch extracted in step S64*b* is delayed to create comparison data (second comparison data) (second delay step) (step S65*b*).

More specifically, a certain time delay is inserted in the transfer of the data of the extracted pattern to create data for comparison with data of a subsequently detected pattern.

Next, the difference between the pattern having a specific repetition pitch extracted in step S64*b* and the second comparison data is calculated (fourteenth calculation step) (step S66*b*).

Next, based on the calculation result of step S66*b*, the presence or absence of a defect is determined (fourth determination step) (step S67*b*).

Here, the determination can be made using two thresholds of an upper bound and a lower bound.

Next, a defect inspection result is determined based on the determination result of step S67*a* and the determination result of step S67*b* (step S68).

Here, if at least one of the determination based on the inspection data and the determination based on the delay data is a determination result representing the presence of a defect, an inspection result representing the presence of a defect can be produced.

Here, the inspection data may be created based on an optical image formed by transmitted light or an optical image formed by reflected light.

According to the embodiment, sufficient inspection sensitivity can be achieved even for an optically unresolvable pattern.

Furthermore, a pattern having a specific repetition pitch can be extracted from the inputted sub-resolution pattern. Based on the extracted pattern having a specific repetition pitch, the presence or absence of a defect can be determined.

Here, by comparison between the extracted patterns having specific repetition pitches, comparison inspection can be performed while mutually canceling the variation of the output level of the patterns.

Thus, in a sub-resolution pattern having a specific repetition pitch, a finer defect can be detected.

[Fourteenth Embodiment]

Next, a pattern inspection method according to a fourteenth embodiment is illustrated.

The pattern inspection method according to the embodiment can be performed in e.g. the inspection section 83 illustrated in FIG. 17.

Figure 29:
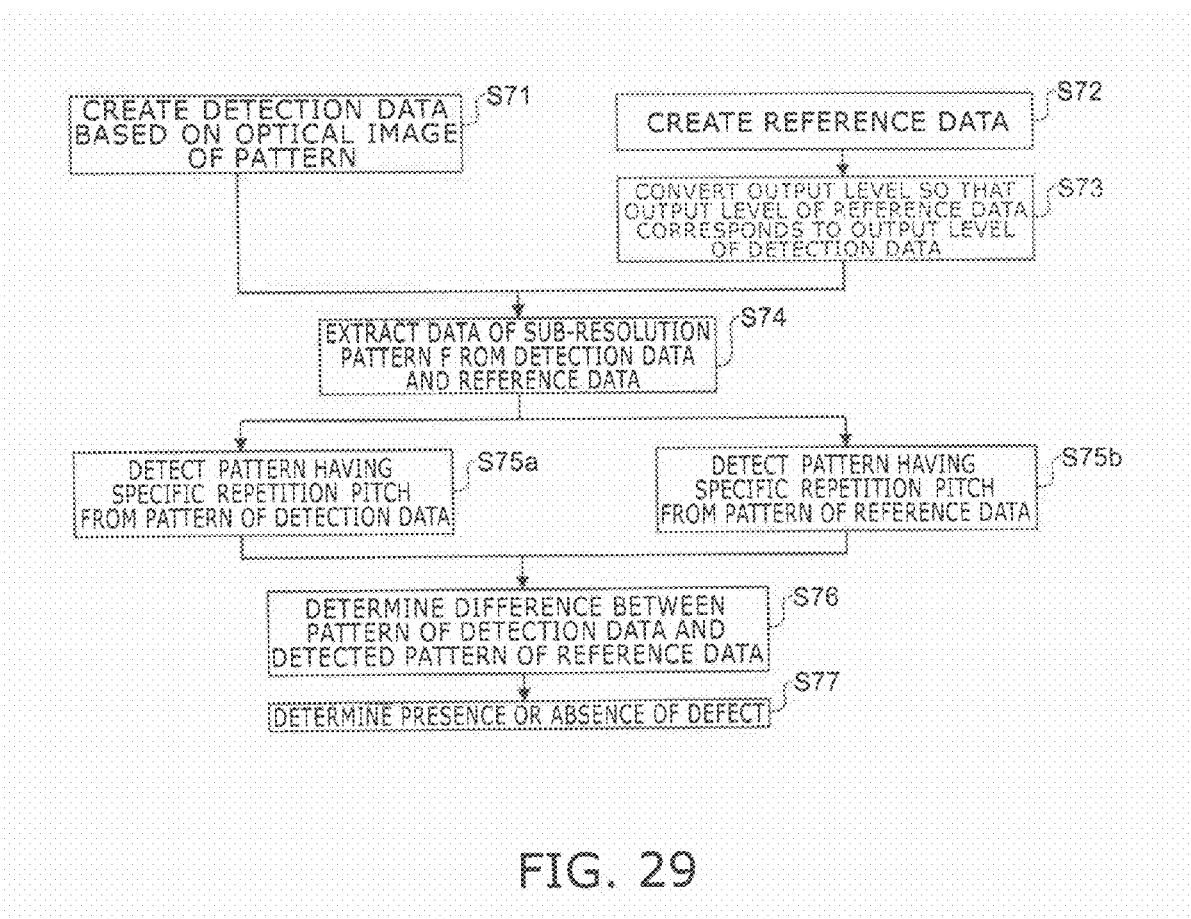
FIG. 29 is a flow chart for illustrating a pattern inspection method according to a fourteenth embodiment.

FIG. 29 is a flow chart for illustrating the pattern inspection method according to the fourteenth embodiment.

First, inspection data is created based on the optical image of a pattern formed on a to-be-inspected object 100 (step S71).

On the other hand, reference data concerning the pattern formed on the to-be-inspected object 100 is created (step S72).

Next, the output level is converted so that the output level of the reference data corresponds to the output level of the inspection data (step S73).

Here, the output level can be converted using a predetermined gradation conversion table. The gradation conversion table can be previously determined by e.g. experiment or simulation.

Next, a sub-resolution pattern is extracted from the inspection data and the reference data whose output level has been converted (eleventh extraction step) (step S74).

Recognition of whether or not the given data is data of a sub-resolution pattern can be performed based on the output level of the reference data. Here, a similar recognition result can be applied to the inspection data corresponding to the reference data.

Next, a pattern having a specific repetition pitch is extracted from the extracted sub-resolution pattern of the inspection data (twelfth extraction step) (step S75*a*).

Furthermore, a pattern having a specific repetition pitch is extracted from the extracted sub-resolution pattern of the reference data (thirteenth extraction step) (step S75*b*).

Here, the extraction of the pattern can be performed by correlation calculation (pattern matching) using a fixed template or the aforementioned variable template.

Next, the difference between the data of the pattern of the inspection data extracted in step S75*a* and the data of the pattern of the reference data extracted in step S75*b* is calculated (fifteenth calculation step) (step S76).

Next, based on the value calculated in step S76, the presence or absence of a defect is determined (step S77).

Here, the determination can be made using two thresholds of an upper bound and a lower bound. If at least one of the determinations using two thresholds of the upper bound and the lower bound is a determination result representing the presence of a defect, an inspection result representing the presence of a defect can be produced.

Furthermore, the inspection data may be created based on an optical image formed by transmitted light or an optical image formed by reflected light.

According to the embodiment, sufficient inspection sensitivity can be achieved even for an optically unresolvable pattern.

Furthermore, a pattern having a specific repetition pitch can be extracted from the inputted sub-resolution pattern. Based on the extracted pattern having a specific repetition pitch, the presence or absence of a defect can be determined.

Here, by comparison between the extracted patterns having specific repetition pitches, comparison inspection can be performed while mutually canceling the variation of the output level of the patterns.

Thus, in a sub-resolution pattern having a specific repetition pitch, a finer defect can be detected.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A pattern inspection apparatus comprising:
a first inspection data creation section configured to create first inspection data based on an optical image of a pattern formed on a to-be-inspected object;
a first reference data creation section configured to create first reference data concerning the pattern;
a first gradation conversion section configured to convert an output level so that the output level of the first reference data corresponds to the output level of the first inspection data;
a third level difference calculation section configured to calculate a difference between the first inspection data and the first reference data whose output level has been converted;
an average level difference calculation section configured to calculate an average of values calculated by the third level difference calculation section, the average in a region of N pixels x N pixels in the first inspection data being calculated; and
a distribution collect section configured to collect the averages calculated by the average level difference calculation section over an entire inspection region of the to-be-inspected object.

2. The apparatus according to claim 1, further comprising:
a sixth determination section configured to determine presence or absence of a defect based on the average calculated by the average level difference calculation section.

3. The apparatus according to claim 1, further comprising:
a fourth recognition section configured to recognize whether or not the first inspection data and the first reference data inputted to the fourth recognition section are data concerning an image of a sub-resolution pattern; and
a fourth extraction section configured to extract data of the sub-resolution pattern from the first inspection data and the first reference data based on a recognition result of the fourth recognition section.

4. A pattern inspection apparatus comprising:
a first inspection data creation section configured to create first inspection data based on an optical image of a pattern formed on a to-be-inspected object;
a first delay section configured to create first delay data by delaying the first inspection data;
a first recognition section configured to recognize whether or not the first inspection data and the first delay data inputted to the first recognition section are data concerning an image of a sub-resolution pattern;

a first extraction section configured to extract data of the sub-resolution pattern from the first inspection data and the first delay data based on a recognition result of the first recognition section;

a first pattern extraction section configured to extract data of a pattern having a specific repetition pitch from the extracted data for the first inspection data;

a fourth delay section configured to create first comparison data by delaying the data extracted by the first pattern extraction section;

a fourth level difference calculation section configured to calculate a difference between the data extracted by the first pattern extraction section and the first comparison data;

a seventh determination section configured to determine presence or absence of a defect based on a calculation result of the fourth level difference calculation section;

a second pattern extraction section configured to extract data of a pattern having a specific repetition pitch from the extracted data for the first delay data;

a fifth delay section configured to create second comparison data by delaying the data extracted by the second pattern extraction section;

a fifth level difference calculation section configured to calculate a difference between the data extracted by the second pattern extraction section and the second comparison data;

an eighth determination section configured to determine presence or absence of a defect based on a calculation result of the fifth level difference calculation section; and a third logic OR calculation section configured to calculate logic OR of a determination result of the seventh determination section and a determination result of the eighth determination section.

5. A pattern inspection apparatus comprising:

a first inspection data creation section configured to create first inspection data based on an optical image of a pattern formed on a to-be-inspected object;

a first reference data creation section configured to create first reference data concerning the pattern;

a first gradation conversion section configured to convert an output level so that the output level of the first reference data corresponds to the output level of the first inspection data;

a fourth recognition section configured to recognize whether or not the first reference data inputted to the fourth recognition section is data concerning an image of a sub-resolution pattern;

a fourth extraction section configured to extract data of the sub-resolution pattern from the first inspection data and the first reference data based on a recognition result of the fourth recognition section;

a third pattern extraction section configured to extract data of a pattern having a specific repetition pitch from the data for the first inspection data and the data for the first reference data extracted by the fourth extraction section;

a sixth level difference calculation section configured to calculate a difference between the data of the pattern having the specific repetition pitch for the first inspection data and the data of the pattern having the specific repetition pitch for the first reference data extracted by the third pattern extraction section; and a ninth determination section configured to determine presence or absence of a defect based on a calculation result of the sixth level difference calculation section.

* * * * *